US012692352B2

(12) United States Patent (10) Patent No.: US 12,692,352 B2
Foo et al. (45) Date of Patent: *Jul. 28, 2026

(54) DETECTABLE AND MULTI DETECTABLE ARTICLES

(71) Applicant: SKINPROTECT CORPORATION SDN BHD, Klang (MY)

(72) Inventors: Khon Pu Foo, Klang (MY); Chin Keong Lim, Klang (MY); Nurshamila Binti Shaari Balakrishna, Klang (MY)

(73) Assignee: SKINPROTECT CORPORATION SDN BHD, Selangor (MY)

( * ) Notice: Subject to any disclaimer, the term of this patent is extended or adjusted under 35 U.S.C. 154(b) by 0 days.

This patent is subject to a terminal disclaimer.

(21) Appl. No.: 16/919,889

(22) Filed: Jul. 2, 2020

(65) Prior Publication Data

US 2020/0385537 A1 Dec. 10, 2020

Related U.S. Application Data

(62) Division of application No. 16/705,639, filed on Dec. 6, 2019, now abandoned.

(30) Foreign Application Priority Data

Dec. 7, 2018 (AU) ................................. 2018904670

(51) Int. Cl.
*C08K 3/22* (2006.01)
*A61B 42/10* (2016.01)
(Continued)

(52) U.S. Cl.
CPC ................ *C08J 5/18* (2013.01); *G01N 33/02* (2013.01); *C08J 2307/02* (2013.01);
(Continued)

(58) Field of Classification Search
None
See application file for complete search history.

(56) References Cited

U.S. PATENT DOCUMENTS 2,328,105 A * 8/1943 Strobino ................. G21F 1/125
524/439
4,253,886 A * 3/1981 Aonuma ................... B22F 1/02
148/105
(Continued)

FOREIGN PATENT DOCUMENTS

CN 101022931 A 8/2007
CN 202489243 U 10/2012
(Continued)

OTHER PUBLICATIONS

The IRM Quarterly, Fall 2000, vol. 10, No. 3, Institute for Rock Magnetism (Year: 2000).*

(Continued)

*Primary Examiner* — Frank J Vineis
*Assistant Examiner* — Nicole T Gugliotta
(74) *Attorney, Agent, or Firm* — WHDA, LLP

(57) ABSTRACT

This application relates to elastomeric articles such as gloves, compositions for producing the articles and methods for their manufacture. The elastomeric articles contain particles for detectability of the articles (or portions thereof) by metal detectors and/or x-ray detectors. The articles may contain magnetic particles, highly conductive particles, or high atomic mass element-containing particles, and a viscosity modifier to ensure dispersion of the particles throughout the film layer in which the particles are present. The particles may be magnetic particles specifically, and may be coated by a corrosion inhibitor coating.

16 Claims, 4 Drawing Sheets

(51) Int. Cl.

| | |
|---|---|
| *B29C 41/14* | (2006.01) |
| *B32B 25/02* | (2006.01) |
| *B32B 25/12* | (2006.01) |
| *B32B 25/18* | (2006.01) |
| *C08J 5/02* | (2006.01) |
| *C08J 5/18* | (2006.01) |
| *C08K 3/08* | (2006.01) |
| *C08K 3/11* | (2018.01) |
| *C08K 9/10* | (2006.01) |
| *C08L 9/04* | (2006.01) |
| *G01N 33/02* | (2006.01) |

(52) U.S. Cl.
CPC ........ *C08J 2311/02* (2013.01); *C08J 2319/02* (2013.01); *C08K 2003/0812* (2013.01); *C08K 2003/0856* (2013.01); *C08K 3/22* (2013.01); *C08K 2003/2258* (2013.01); *C08K 2003/2275* (2013.01); *C08K 9/10* (2013.01); *C08K 2201/001* (2013.01); *C08K 2201/01* (2013.01)

(56) References Cited

U.S. PATENT DOCUMENTS

| | | | |
|---|---|---|---|
| 4,684,490 A | 8/1987 | Taller et al. | |
| 5,380,783 A | 1/1995 | Satake et al. | |
| 5,554,673 A | 9/1996 | Shah | |
| 5,922,482 A | 7/1999 | De Ricci et al. | |
| 7,000,295 B2 | 2/2006 | Andrews | |
| 7,122,593 B2 | 10/2006 | Lucas et al. | |
| 7,635,733 B2 | 12/2009 | Lucas et al. | |
| 8,334,524 B2 | 12/2012 | DeMeo et al. | |
| 9,808,039 B2 | 11/2017 | Enomoto et al. | |
| 10,546,664 B2 | 1/2020 | Yonekura et al. | |
| 2004/0154072 A1 | 8/2004 | Connor | |
| 2004/0262546 A1 | 12/2004 | Thiess et al. | |
| 2005/0119387 A1 | 6/2005 | Lucas et al. | |
| 2005/0211930 A1 | 9/2005 | DeMeo et al. | |
| 2007/0083977 A1 | 4/2007 | Lucas et al. | |
| 2007/0298184 A1 | 12/2007 | Connor | |
| 2008/0128658 A1 | 6/2008 | Jungermann et al. | |
| 2010/0056669 A1* | 3/2010 | Bailey | B29B 9/16 523/201 |
| 2010/0124644 A1 | 5/2010 | Hein et al. | |
| 2010/0239864 A1* | 9/2010 | Handa | C09D 125/14 427/127 |
| 2011/0231983 A1 | 9/2011 | Chan | |
| 2015/0132574 A1 | 5/2015 | Aldridge et al. | |
| 2015/0272245 A1 | 10/2015 | Khor et al. | |
| 2016/0150840 A1 | 6/2016 | Enomoto et al. | |
| 2016/0159992 A1* | 6/2016 | Foo | C08K 3/30 428/480 |
| 2017/0218142 A1* | 8/2017 | Foo | A61L 31/049 |
| 2018/0193237 A1* | 7/2018 | Foo | A41D 13/087 |
| 2021/0088959 A1 | 3/2021 | Schmid et al. | |

FOREIGN PATENT DOCUMENTS

| | | | | |
|---|---|---|---|---|
| CN | 108604474 B | 3/2020 | | |
| EP | 0 773 455 A1 | 5/1997 | | |
| EP | 1 864 788 A2 | 12/2007 | | |
| EP | 1 365 665 B1 | 4/2009 | | |
| EP | 3 404 670 A1 | 11/2018 | | |
| GB | 2372934 A * | 9/2002 | ........ A41D 19/0055 |
| JP | 2003-247961 A | 9/2003 | | |
| JP | 2005-519294 A | 6/2005 | | |
| JP | 2008-189788 A | 8/2008 | | |
| JP | 2009-120974 A | 6/2009 | | |
| JP | 2013/101080 A | 5/2013 | | |
| JP | 7018888 B2 | 2/2022 | | |
| WO | 99/20685 A1 | 4/1999 | | |
| WO | WO-02068168 A2 * | 9/2002 | ............ B29C 33/62 |
| WO | 03/065832 A2 | 8/2003 | | |
| WO | 2006/026823 A1 | 3/2006 | | |
| WO | 2010/003530 A1 | 1/2010 | | |
| WO | 2013/0153390 A1 | 7/2013 | | |
| WO | 2017/065599 A1 | 4/2017 | | |

OTHER PUBLICATIONS

Puspita et al., "Phase Transition of Fe3O4 Magnetic Material Based on Observation of Cure Temperature and Hysteresis Curve: Micromagnetic Simulation Study," European Journal of Applied Physics, vol. 3, Issue 2, Mar. 2021. (Year: 2021).*

Cestus® Armored Gloves (https://cestusline.com/blogs/news/glove-sizing-guide) (Dec. 24, 2020). (Year: 2020).*

Ries, B., "What food processors should know: metal detection vs. X-ray inspection", ThermoScientific, White Paper (2017) (in English; 3 pages).

Database WPI Week 201732, Thomson Scientific, London, AN 2017-259964, XP-002798612 (2017) (in English; cited in counter-part European Patent Appl. No. 19214292).

Office Action dated Mar. 10, 2021, issued in U.S. Appl. No. 16/705,639 (in English; 22 pages; w/ PTO-892 form and returned PTO/SB/08a form).

Ralphs, "50PCS Disposable Plastic Spoons Chinese Asian Soup Spoon Kitchen Dessert Serving", available at https://www.ralphs.com/p/50pcs-disposable-plastic-spoons-chinese-asian-soup-spoon-kitchen-dessert-serving/0009636221198 (in English; 2021; in U.S. Appl. No. 16/919,889 and U.S. Appl. No. 16/705,639).

"What Material is Silicone: Rubber, Latex, or an Elastomer?", Silicon Engineering Ltd., available at https://silicone.co.uk/news/is-silicone-a-rubber/ (in English; 2016; in U.S. Appl. No. 16/919,889 and U.S. Appl. No. 16/705,639).

Zhu et al., "Silica stabilized iron particles toward anti-corrosion magnetic polyurethane nanocomposites," RSC Advances, vol. 2, pp. 1136-1143 (2012) (in English; in U.S. Appl. No. 16/705,639).

Office Action dated Sep. 27, 2021, issued in co-pending U.S. Appl. No. 16/705,639 (in English; 27 pages; w/ PTo-892 and returned PTO/SB/08).

Tadic M., et al., "Synthesis, morphology, microstructure and magnetic properties of hematite submicron particles", Journal of Alloys and Compounds, vol. 509, pp. 76389-7644 (Apr. 30, 2011) (in English; 6 pages; cited in co-pending U.S. Appl. No. 16/705,639).

Office Action dated Jan. 24, 2022, issued in counterpart CN application No. 201980014525.1, with English translation. (67 pages).

Non-Final Office Action dated Apr. 14, 2022, issued in U.S. Appl. No. 16/705,639. (18 pages).

Final Office Action dated Nov. 28, 2022, issued in U.S. Appl. No. 16/705,639. (32 pages).

Non-Final Office Action dated Sep. 5, 2024, issued in U.S. Appl. No. 16/705,639. (18 pages).

* cited by examiner (1) B (2) A (3) A (1) B (2) A

FIG.1(G)              FIG.1(H)

I    III    IV   V   II

DETECTABLE AND MULTI DETECTABLE ARTICLES

CROSS-REFERENCE TO RELATED APPLICATIONS

This application claims divisional status from U.S. Ser. No. 16/705,639, filed Dec. 6, 2019, which in turn claims priority to Australian Patent Application No. 2018904670, filed on Dec. 7, 2018. The entirety of each of these related applications is hereby incorporated by reference.

FIELD

The present application relates to elastomeric articles that are detectable by detection devices that may be used in industry (e.g. the food industry) to detect foreign matter. The articles may be in the form of wearable articles, such as gloves and finger cots. The articles may be detectable by two or more classes of detection devices (i.e. they may be "multi-detectable"). The detection devices for detection of the articles or portions thereof may be x-ray detectors and metal detectors.

BACKGROUND

In the food production industry and other manufacturing industries, it is important to avoid foreign object contamination of the products being handled or passing through the production line. Systems for checking a food product during production, and in packaged form ready for sale to consumers, need to take into account the wide range of equipment components and tools used in the preparation of the food product. Thin film disposable gloves and finger cots are used extensively by food handlers in food production lines and in other manufacturing industries to avoid food contamination through contact with the hands of the food handler. Accordingly, it is important in the food industry to ensure that gloves, finger cots, and any broken-away pieces thereof, do not contaminate food products and processing streams.

In such industries, detectors are already in use to detect for foreign objects in food products. Metal detectors are used to detect for magnetic metal objects such as screws, metal shavings and other metallic objects that may unintentionally fall into a food product.

It has previously been proposed to include fine metal particles, such as ferrous metal particles, in the polymer compositions used to make disposable polymeric gloves and finger cots. The inclusion of such particles has the potential to allow for the gloves, finger cots, or portions thereof—i.e. contaminants—to be detected by metal detectors. However, there are a number of problems associated with this.

Firstly, there can be problems with the detectability of the low levels of metallic particles in the contaminant. That is, the sensitivity of the detectors, combined with the small amount of metal particles, may be such that the contaminant escapes detection, particularly when only a small portion of the glove or finger cot is present in the food product. Increasing the size and/or percentage amount of the particles in the composition used to make the glove/finger cot can lead to processing difficulties during glove/finger cot production. Increasing the sensitivity of the detector is an alternative option to increasing the particle size or loading, but this may not be possible because of interference caused by the nature of the food product and/or the surrounding electromagnetic field within the detector.

A second problem is that foodstuffs prepared in wet conditions, or foodstuffs that are high in sodium or packaged/wrapped in metal foil packaging, can hinder the ability for a metal detector to detect the metallic particle-containing contaminant. For example, if the packaging for the food product is a metal foil laminate, then the metal detector will be unable to distinguish between the metal-containing contaminant (glove, finger cot or portion thereof), and the packaging.

While there have been some glove products described in the art that are reportedly metal-detectable, such products tend to have a high thickness to allow for a sufficient loading of detectable particles, or to provide the required tensile strength of the glove (noting that thicker films tend to be stronger, and counteract the weakening of the film caused by the loading of metal particles). This is particularly a problem for PVC-type metal-detectable food handling gloves—such metal-detectable PVC gloves are commonly around 7 grams in weight, compared to a non-detectable glove weight of about 4 grams. Such higher weight/thicker PVC-type glove products tend to have lower "tactile sensitivity" for the wearer of the product (the gloves are too thick to feel through the glove). The food industry does not generally accept high cost products for food handling, due to low margins in the industry. In addition, gloves that have low sensitivity are often commercially unsuccessful.

Another problem that can arise relates to the distribution of the metal-detectable particles in the article, and in the composition from which the articles are produced. Heavy particulate matter included into a composition for producing dip-formed articles tends to settle in the composition and/or agglomerate into clumps. This can result in poor distribution of the particulate matter in the final product. This problem can be more pronounced for certain types of elastomeric materials—particularly latex materials of the non-PVC type.

Food processing facilities may use different types of detectors at different locations; for example, metal detectors may be placed in the raw material section while x-ray detectors are installed in the finished goods section to detect foreign matter. The consequence of this is that different glove types—one suited to metal detectability and the other suited to x-ray detection—need to be worn by employees working in different sections of the production line, or those employees working across the full food production line may be required to constantly change glove types depending on their location as they move around the business. It would be advantageous in relation to some embodiments for there to be glove/finger-cot products that meet the needs of both types of detection systems, to avoid this problem.

It is an object of the present invention to provide new elastomeric articles that have an improved detectability, or that have improved overall properties or distribution of detectable particles in the product, or to at least provide a useful alternative to existing products on the market.

SUMMARY

According to the present invention, there is provided an elastomeric article comprising an elastomeric film containing one or more film layers, and at least two types of particles including:
- (a) magnetic particles and/or conductive particles having electrical conductivity of at least $3.0 \times 10^7$ S/m at 20° C., and
- (b) particles containing one or more high atomic mass elements with an atomic mass of at least 132,
dispersed throughout at least one of said film layers.

Such articles and portions thereof having a film volume of at least 0.08 mm³ are multi-detectable. The articles or portions of a particular minimum size are capable of detection by either or both of metal and x-ray detectors. The fact that the articles can be detected by each type of detection system allows the article (or a portion thereof) to be detected by one form of detector when there are impediments to the detection of the article by a second form of detector (for example, when metal detection is obscured by metal foil laminate packaging). The detectors in this regard are of a type suitable for conducting foreign matter detection in a processing line, such as a food production line.

The applicant found that by incorporating two types of particles in the elastomeric film, within one or more of the film layers, they were able to provide a sufficiently high degree of detectability by each of two forms of detectors, and thereby provide elastomeric articles having greater utility in a wide range of applications. The magnetic or conductive particles are capable of detection by metal detectors. Whilst some forms of magnetic particles, such as ferrite particles, are theoretically also detectable by X-ray, the ability to detect contaminants containing such ferrite particles may be obscured or prevented by food packaging material (e.g. metal foil). However, by incorporating particles containing one or more high atomic mass elements (e.g. barium or tungsten), the applicant found it was possible to detect contaminants containing the combination of particles even when packaged in metal foil, due to the manner of incorporation and high detectability of the high atomic mass element particles using x-ray detection.

After the applicant had identified the desirability of combining the two different types of particles in elastomeric articles, the applicant was unaware as to whether it would be possible to incorporate such particles in elastomeric films in a manner that would not severely impact on the film properties, particularly given the loadings that might be required to provide effective detectability. Furthermore, with particles of high density such as the magnetic particles, the conductive particles, and/or the particles with high atomic mass elements, there was also the potential problem of ineffective distribution through the elastomeric film-forming composition, such that even if the particles could be included in the liquid latex composition, they might not be picked-up within the elastomeric film layer during article production, such as dip-formation. Moreover, any modifications that would need to be made to the formulation or manufacturing method would need to be viable from a variety of perspectives, including final film properties, colour, fluidity of mixtures, strength of film, softness of film, flexibility of film (as indicated by elongation), and so forth. It was not readily predictable or expected that the desired objective of multi-detectability would be achievable, while maintaining acceptable film properties, particularly for a glove product.

Through the use of one or more of the techniques and composition components described herein, the applicant was able to produce products that are detectable through at least one forms of detector (metal and/or X-ray), regardless of whether the product (e.g. packaged food product) being scanned for potential contaminants is metal-containing or not.

According to the present invention, there is also provided an elastomeric film-forming composition comprising:
(a) magnetic particles, and/or conductive particles having electrical conductivity of at least $3.0 \times 10^7$ S/m at 20° C., and
(b) particles containing one or more high atomic mass elements with an atomic mass of at least 132,
dispersed throughout the composition.

In preferred embodiments, the elastomeric film-forming composition further comprises a viscosity modifier. The test work completed by the applicant demonstrates the efficacy of a viscosity modifier in ensuring that the particles incorporated into the composition remain well dispersed throughout the composition, and are picked-up into the elastomeric film layer (particularly during dip-production) rather than settling out of solution or pooling in an uneven manner within the film layer prior to curing.

The particles in the elastomeric articles may be coated particles or uncoated particles. Further detail on the optional coating of the particles in the multi-detectable articles is provided below.

According to the present invention, there is also provided a method of manufacturing an elastomeric article, the method comprising:
incorporating (a) magnetic particles, and/or conductive particles having electrical conductivity of at least $3.0 \times 10^7$ S/m at 20° C., and (b) particles containing one or more high atomic mass elements (with an atomic mass of at least 132) into one or more elastomeric film-forming compositions, and
dipping a former into the one, or each of, said one or more elastomeric film-forming compositions, to produce an article comprising one or more film layers, in which (a) the magnetic particles and/or conductive particles and (b) the particles containing one or more high atomic mass elements are dispersed throughout at least one of said film layers.

In the above outline of the method of manufacture, it will be understood that, where more than one elastomeric film-forming composition is contemplated, the different types of particles used can be incorporated into separate compositions (so as to be dispersed throughout that composition as the single particle type in that composition), or the particles can be distributed in combinations of two (or three) particle types for any film layer composition. There are several alternative combinations that can be used to create a film with the particles distributed throughout a particular film layer. As one example, where there are two types of particles used (e.g. magnetic particles and high atomic mass element particles, or conductive particles and high atomic mass particles), and a two-layer film is produced, each of those particle types may be present in separate layers of the two-layered film, or the particles can be combined into one film layer (with another layer that also contains the same particle combination, or one particle type only, or no particles). In an alternative example, the particles of each type (two or three types) may be incorporated into the same elastomeric film-forming composition, for forming a film layer containing a mixture or combination of those particles throughout. There may be additional layers containing one of the particle types, two particle types, three particle types, or no particles of any of the three categories described. If all three particle types are incorporated into the film, the particles may be included separately into each of three separate layers of a three-layered film, or combinations of the particles may be included in one or both layers of a two-layered film or a single-layered film, or otherwise.

To aid further discussion, the particles of grouping (a) may be divided into the two sub-groupings, being particles (a(i))—the magnetic particles, and (a(ii))—the conductive particles. As noted previously, either or both of these particle types may be used, together with particles (b).

Where the method involves the incorporation of two particle types (i.e. (a(i)) and (b) or (a(ii)) and (b)), or all three particle types (a(i)), (a(ii)) and (b), into the same layer, or multiple layers, the method may comprise:

dipping a former into an elastomeric film-forming composition as described above (containing particles (a(i)) and/or (a(ii)), and (b)); and curing the elastomeric film-forming composition on the former so as to produce the elastomeric article.

The dipping step may be performed once or multiple times, to produce multiple layers of film that contain the particles (a(i)) and/or (a(ii)), and (b). One or more additional dipping steps, into film-forming compositions that do not contain particles (a(i)), (a(ii)) and (b) can also be performed.

This dip production technique is particularly suited to the production of wearable elastomeric articles such as elastomeric gloves and finger cots, and elastomeric footwear (such as booties, socks or the like). Such articles are suitably dipped articles. The method involves dipping a former, having the shape of the intended object (such as a hand-shaped former, finger-shaped former, or foot-shaped former), into the elastomeric film-forming composition, with any preceding or subsequent steps commonly used in dip-formation of products. However, it is noted that other elastomeric articles may be produced using other techniques, such as extrusion.

In embodiments of the invention, the wearable articles as described above, such as the glove forms of the articles (but also the footwear forms of the articles), may additionally or alternatively function as radiation-shielding articles, as a consequence of their radiation attenuation properties. Accordingly, the present application provides for the use of the elastomeric articles described above as radiation-shielding wearable articles. The present application also provides for the use of the elastomeric articles as metal detectable, x-ray detectable and radiation-attenuating articles. The present application further provides for the use of the composition described above for the production of multi-detectable articles that are detectable by metal detector and x-ray detector.

During the process of developing the above articles, compositions and methods, the applicant has identified additional challenges for the production of detectable articles that can apply to articles that contain certain types of particles. The applicant has developed a range of solutions for addressing those problems, which can apply more generally to elastomeric articles that contain one class of particles (e.g. particles (a(i))) that provide detectability to the article), optionally with additional classes of particles.

One problem that arises is that some types of detectable particles can be reactive and prone to corrosion, especially in the presence of moisture and/or oxygen. This has particular application when corrodible metallic particles are used as the particles of types (a(i)), (a(ii)) or (b), and particularly to some classes of particles of type (a(i))—the magnetic particles or (a(ii))—the highly conductive particles. To those familiar with the art, the formation of an elastomeric article commonly involves water-based systems (e.g. water-based elastomeric film-forming compositions, for dip-formation of articles) which would be detrimental to the stability of the corrodible metallic particles during production or in the final product.

The applicant has found that corrosion of such particles can be reduced or avoided by introducing a layer of protection surrounding the particles (the particle surface), which reduces, delays or avoids the corrosion of the particles. In particular, the particles may comprise a corrosion inhibitor coating. In an alternative solution, the film may be modified to contain a non-coating inclusion of corrosion inhibitor. The manner of inclusion of the corrosion inhibitor in the film needs to be such as to create an environment in the film that inhibits corrosion of the corrodible particles. The materials that have highly magnetic properties (to provide high metal detectability) that are most desired to be incorporated into elastomeric articles for enhanced magnetic detectability tend to be the more corrodible materials—so the proposals outlined above address this potential problem. Coating of such particles, or incorporation of a non-coating inclusion of a corrosion inhibitor in the film containing the particles, allows for the elastomeric articles (such as gloves) to be fully produced in various colours. This is possible because corrosion (leading to article discoloration which may be more evident in lighter-coloured products) is minimised or avoided. Additionally, other improvements may arise from the use of a coating on the particles such as improvements in dispersion of the particles throughout the film-forming composition, and improvements in the uniform distribution of particles across the article.

Following from this, the present application provides an elastomeric article comprising an elastomeric film containing one or more film layers, wherein at least one film layer comprises magnetic particles coated by a corrosion inhibitor, dispersed throughout the film layer.

The corrosion inhibitor creates a protective particle coating that prevents or reduces contact between the magnetic particle core and water and/or oxygen that comes into contact with the particles in the film layer during production or in use.

The present application also provides an elastomeric article comprising an elastomeric film containing one or more film layers, wherein at least one film layer comprises magnetic particles and a corrosion inhibitor dispersed throughout the film layer, wherein the corrosion inhibitor inhibits corrosion of the magnetic particles in the film.

Combining these options together, the present application further provides an elastomeric article comprising an elastomeric film containing one or more film layers, wherein at least one film layer comprises magnetic particles dispersed throughout the film layer, wherein the magnetic particles are coated by a corrosion inhibitor, and/or a corrosion inhibitor is dispersed throughout said film layer containing the magnetic particles.

The elastomeric article containing the magnetic particles and corrosion inhibitor (as a coating or non-coating inclusion) may further comprise:

conductive particles having electrical conductivity of at least $3.0 \times 10^7$ S/m at 20° C., and/or particles containing one or more high atomic mass elements with an atomic mass of at least 132, dispersed throughout at least one of said film layers.

The conductive particles and/or the high atomic mass element particles may be uncoated or coated particles. The coating may be a corrosion inhibitor coating.

Another problem identified by the applicant when producing the new products related to the ability to distribute the detectable particles (whether they are a single type of particles or a mixture of particle types) within the elastomeric film-forming composition, so as to be well distributed throughout the composition and thereafter remain well-distributed throughout the final film product. As one example, particles with good magnetic detectability tend to be very heavy and to settle and/or clump in the composition. The applicant tried a range of approaches to distribute the particles effectively in the film-forming compositions, for producing dipped-articles, and many attempted approaches failed. A problem faced was that it was not possible to use a range of thickening agents in quantities that provided the suspension properties, while avoiding gumming or processing problems in the manufacturing line. Non-pseudoplastic thickening agents also tended to create overly thick layers of elastomeric film-forming composition on the formers (e.g. glove-shaped formers), which adversely impacted on the final product weight, thickness, sensitivity and other properties.

The applicant's solution to this problem was to select a particular class of viscosity modifiers, being the pseudoplastic viscosity modifiers, to address this problem. These viscosity modifiers could be used to suspend the particles effectively, while avoiding processing problems with dip formation of the articles. The viscosity modifiers also allowed for the particles to remain suspended for a sufficient period of time for effective commercial operations. Significant work had to be completed by the applicant to determine suitable amounts of the viscosity modifiers to achieve a required balance of properties, both in terms of manufacturing practicalities, and glove properties (thickness, distribution of particles, tensile strength, modulus, etc.)

According to this aspect, the present application provides an elastomeric article comprising an elastomeric film containing one or more film layers, wherein at least one film layer comprises:

at least one type of particles selected from (a(i)) magnetic particles, (a(ii)) conductive particles having electrical conductivity of at least $3.0 \times 10^7$ S/m at 20° C. and/or (b) particles containing one or more high atomic mass elements dispersed throughout the film layer, and a pseudoplastic viscosity modifier for achieving the dispersion of said particles throughout the film layer.

The particles included in the elastomeric article of this aspect of the application may be magnetic particles (a(i)) alone. The particles may be magnetic particles in combination with either or both of particles (a(ii)) and (b). The particles may be coated or uncoated particles, as described above. Preferred features of the pseudoplastic viscosity modifier, and preferred amounts of that component, are as described in further detail below.

The present application similarly provides an elastomeric film-forming composition comprising:

at least one type of particles selected from (a(i)) magnetic particles, (a(ii)) conductive particles having electrical conductivity of at least $3.0 \times 10^7$ S/m at 20° C. and/or (b) particles containing one or more high atomic mass elements, and a pseudoplastic viscosity modifier for dispersing said particles throughout the composition.

The present application further provides a method for the production of the above-described elastomeric article, the method comprising:

combining at least one type of particles selected from (a(i)) magnetic particles, (a(ii)) conductive particles having electrical conductivity of at least $3.0 \times 10^7$ S/m at 20° C. and/or (b) particles containing one or more high atomic mass elements, and a pseudoplastic viscosity modifier in an elastomeric article-forming composition so as to effect dispersion of said particles throughout the composition;

dipping a former into said elastomeric film-forming composition; and curing the elastomeric film-forming composition on the former so as to produce the elastomeric article.

The method may further comprise the step of:

stirring the elastomeric film-forming composition in a dipping tank so as to maintain the viscosity of the composition during dipping of the former into the composition at a level that is lower than that for the unstirred elastomeric film-forming composition.

Given that production methods are continuous, the stirring continues during the dipping process, so as to maintain a relatively low-viscosity composition in the dipping tank during dipping.

Notable features of the articles, compositions and methods are described throughout the detailed description.

BRIEF DESCRIPTION OF THE DRAWINGS

The present inventions will now be described in further detail with reference to the Figures which illustrate non-limiting examples of aspects of the inventions.

FIGS. 1(A), 1(B), 1(C), 1(D), 1(E), 1(F), 1(G) and 1(H) contain schematic illustrations of eight alternative embodiments of the invention, containing magnetic and/or conductive particles (indicated as solid dots) and particles containing one or more high atomic mass elements (indicated as hollow dots) present in different arrangements in a layered elastomeric film. The film layers are marked A for those layers containing the particles, and B for those layers that are free of particles.

DETAILED DESCRIPTION

Figures 1A, 1B, 1C, 1D, 1E, 1F:
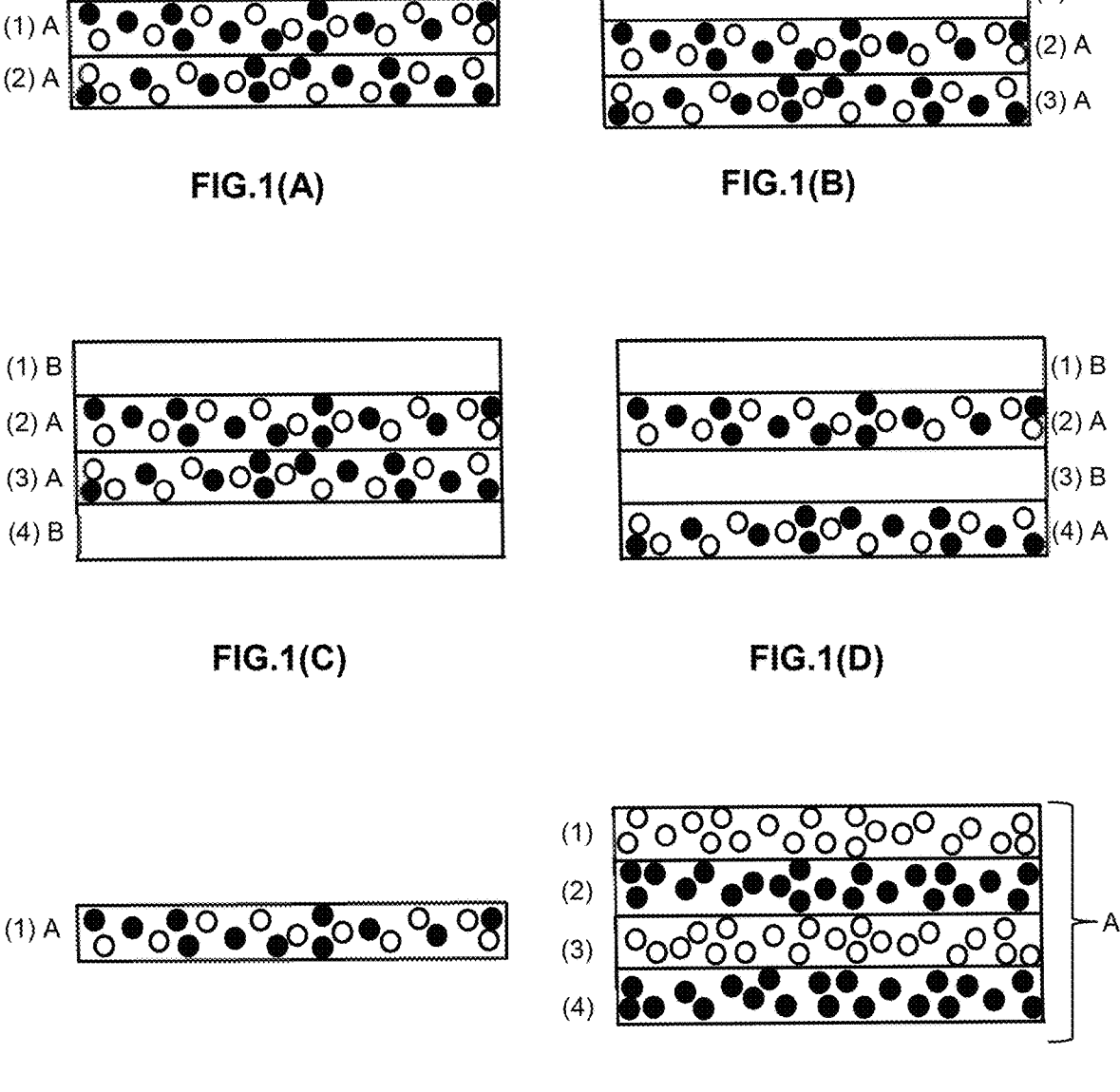

The synthetic elastomeric articles and methods of manufacture are described in further detail in this section.

Unless indicated to the contrary, the description of general features of the articles of the invention, corresponding film-forming compositions and methods for their production apply equally to:

articles containing the combination of particles (a) and (b), articles containing corrosion inhibitor-coated magnetic particles or magnetic particles with a non-coating inclusion of a corrosion inhibitor, and articles containing one particle type only (e.g. magnetic particles, which are coated or uncoated), with a pseudoplastic viscosity modifier.

Elastomeric Articles

Examples of elastomeric articles that are applicable to the present invention include wearable articles, such as gloves, finger cots, head-coverings and footwear (encompassing socks, booties and so forth). The gloves may be gloves for food contact, food processing and biotechnical applications. The invention also extends to other glove types including disposable gloves, surgical gloves, examination gloves, industrial gloves, laboratory gloves, irradiation gloves, industrial gloves, clean room gloves for electronic industries, household gloves and so forth. The articles are suitably disposable elastomeric articles. Disposable elastomeric articles are characterised by their low thickness (i.e. thin film), contributing to a low overall weight and low cost, making the products suitable for disposal after a period of use. Whilst the elastomeric articles are preferably disposable elastomeric articles—or in other words, self-supported film articles, the same formulations can be used for the production of supported articles. An example of a supported article is a supported glove. Such gloves have a liner, such as a knitted or woven liner, which is dipped into the elastomeric film-forming composition to create a layer or layers of elastomeric film with the liner embedded therein. Supported articles having the effective combination of particles (a) and (b), incorporated throughout the elastomeric film, may suit a variety of applications where a high degree of sensation is not required. The same applies for articles containing corrosion inhibitor-coated magnetic particles, or containing magnetic particles with a non-coating inclusion of a corrosion inhibitor.

The articles may be dipped articles (i.e. articles produced from a dipped elastomeric film, noting that the particles may be incorporated into the articles by dipping or any other suitable technique). In some instances, dip-formed articles are specifically preferred.

The articles may comprise a single layer film, or more than one film layer (i.e. a multilayered film). The number of film layers may be between 1 and 15, such as 1-3 or 1-4 layers. Other coatings such as slip coatings or powder coatings to aid donning may also be present. Furthermore, there may be a coagulant layer or additional polymer coating layers (i.e. additional to the elastomeric film layers). In some embodiments, the gloves are liner-free. In some embodiments, the gloves are thin-film gloves without a metal wire layer.

The thickness of the elastomeric film can, for example, be in the range 0.01-2.0 mm. The lower limit of the range may be 0.01, 0.02, 0.05, 0.1 or 0.2 mm. The upper limit of the thickness range may be 2.0, 1.0, 0.5, 0.4, 0.3, 0.2 or 0.1 mm. Any upper limit and lower limit may be combined to form a range without restriction, provided that the lower limit is less than the upper limit. Exemplary ranges are 0.01-0.3 mm, 0.02-0.2 mm, 0.05-0.10 mm, 0.03-0.08 mm, or 0.05-0.08 mm (for thin or disposable gloves and articles), and 0.2-2.0 mm for thick gloves. The thickness is suitably measured as an "average thickness" for the article. In the case of gloves, the thickness is measured using an average of the thickness measurements taken at three points; cuff, palm and finger of glove. In the case of articles other than gloves, if the article is smaller than a glove (e.g. a fingercot), then a single point of measurement can be taken. In the case of other articles such as footwear or head coverings, 3 points of measurement are taken at three spaced locations, and the average is calculated. In some glove embodiments, the glove may have a weight of about 1-5 grams, such as about 4 grams, or about 3 grams. Higher and lower glove weights may also be produced containing the particles (a) and (b) depending on the purpose for which the glove is to be used. In the case of supported films, the weight of the article may be significantly higher. The same comments regarding film thickness and weight apply for articles containing corrosion inhibitor-coated magnetic particles, or containing magnetic particles with a non-coating inclusion of a corrosion inhibitor. The same comments regarding film thickness and weight also apply for articles containing one of the particle types only (e.g. magnetic particles, which may be coated or uncoated), together with a pseudoplastic viscosity modifier.

When calculating the overall thickness of an elastomeric glove, the standard practice in the industry (as established by the relevant standard D6319) is to measure the thickness of the glove at three points—the cuff, the palm and the finger. The finger thickness is measured 13 mm+/−3 mm from the fingertip; the palm thickness is measured at the centre of the palm, and the cuff thickness is measured at 25 mm+/−5 mm from the cuff edge. The average of the three measurements is taken to establish a glove thickness. Thickness measurements are taken in accordance with the procedure specified in ASTM D3767-03 (Reapproved 2014). In simple terms, the procedure involves measuring the thickness based on the median of three measurements made on each test specimen with a micrometer. The micrometer may be analogue or digital. As an example, a Mitutoyo analog micrometer, model 7301, or a Mitutoyo digital micrometer, model PK-101 may be used.

In spite of the articles containing a significant loading of particles (a) and (b) (with either or both of particles (a(i)) and (a(ii)) present), elastomeric articles having good modulus values at 500% elongation were able to be produced. The elastomeric articles of embodiments of the present application have a modulus at 500% elongation less than 25 MPa, and in the case of some elastomer types (e.g. nitrile), usually less than 18 MPa. The modulus at 500% elongation in some products in accordance with some embodiments of the invention may be less than 25, 20, 18, 17, 16, 15, 14, 13 or 12 MPa. The modulus at 500% elongation may be above 1 MPa, and may in some instances be above 2, 3, 4, 5, 6, 6.5, 7, 7.5 or 8 MPa. The modulus at 500% elongation may be within a range based on one of the upper limits (e.g. 25, 20, 18, 15, 14, 13 or 12) with a lower limit (1, 2, 3, 4, 5, 6, 6.5, 7, 7.5 or 8), examples of which include 1-25, 3-18, 3-20, 3-25, 3-16, 3-15, 3-12, 5-12, and 7-12 MPa. A higher modulus range may be associated with thicker elastomeric films. The modulus at 300% elongation may be at least 1.0 MPa, such as at least 1.5, 2.0, 2.5, 3.0 or 3.5 MPa. The modulus at 300% elongation may be less than 7.0 MPa, such as 6.5 MPa or less or 6.0 MPa or less. The modulus values may be based on the unaged variant, but is preferably based on the aged variant, or both the unaged and aged variants. Having this modulus value for an article such as a glove containing high loadings of the particles of types (a) and (b) in combination (with either or both of particles (a(i)) and (a(ii)) present) provides a suitable degree of softness for glove products for use in food handling and similar applications. These values are particularly surprising to have been achieved for articles that contain 5% by weight (or more, such as 10 wt % or more) of the particles (a) and (b). The same applies for articles containing corrosion inhibitor-coated magnetic particles, or containing magnetic particles with a non-coating inclusion of a corrosion inhibitor. The above values for modulus at 300% and 500% can be achieved for articles containing coated magnetic particles and/or an inclusion of corrosion inhibitor in the film layer containing the magnetic particles. The same comments also apply for articles containing one of the particle types only (e.g. magnetic particles, which may be coated or uncoated), together with a pseudoplastic viscosity modifier. The above values for modulus at 300% and 500% are achievable for those single particle-type containing articles.

The elastomeric articles of embodiments of the present application, such as gloves, have an elongation at break of at least 100%. The elongation at break may be even higher, such as at least 200%, at least 300%, at least 400%, at least 500%, at least 550%, at least 600% or at least 650%. It has been found for elastomeric articles containing the two types of particles, if the elongation at break is above 700%, then the tensile strength might not be sufficiently high. Accordingly in some instances, higher elongations at break are not recommended. The same applies for articles containing corrosion inhibitor-coated magnetic particles, or containing magnetic particles with a non-coating inclusion of a corrosion inhibitor. The same comments also apply for articles containing one of the particle types only (e.g. magnetic particles, which may be coated or uncoated), together with a pseudoplastic viscosity modifier.

In spite of the inclusion of the particles (a) and/or (b) in the articles (with or without corrosion inhibitor), the tensile strength of the articles may be quite high, even for low thickness films. The tensile strength of the films produced and tested was above 8 MPa, above 12 MPa, above 14 MPa, and above 16 MPa. Higher values can also be achieved for some embodiments, with tensile strengths above 18, 20, 22, 25, 27 and 30 MPa being achievable.

The elastomeric glove of the present application preferably also meets or exceeds ASTM D6319-00a for water leakage.

The calculations of weight, thickness, modulus, tensile strength and elongation may be based on a sample of at least 10 gloves.

Particles (a(i)) Magnetic Particles

The magnetic particles are particles formed by materials which have a large susceptibility towards external magnetic field. Suitable magnetic particles include ferromagnetic particles such as those formed of iron, nickel, cobalt and/or gadolinium; ferrimagnetic materials, such as ferrites, magnetite and maghemite; and antiferromagnetics such as hematite, chromium and its oxides. These materials may be present in alloys which may also contain other elements such as aluminium, barium, strontium, zinc, neodymium, yttrium and manganese. In some embodiments, the magnetic particles are free of high atomic mass elements.

The magnetic particles are typically dense particles. The density is typically within the range of 2.0 to 23.0 g/cm$^3$, preferably between 5.0 to 9.0 g/cm$^3$.

The average particle size of particles (a(i)) is suitably less than 5 μm, or less than 2 μm. A suitable mass median diameter (D50) is within the range of 0.5-1.2 μm. The particle size is significant—if the particles are too small, the particles tend to aggregate, which is not desired in the present case as a dispersion throughout the film layer is desired, to retain physical properties of the film and detectability of the article or any portion thereof (above a minimum detectable volume). The particle size should also not be too large to avoid deterioration of film strength apart from rapid particle settling in the film-forming composition. The mass mean diameter is preferably not more than 1.8, 1.6, 1.4 or 1.2 μm. The mass mean diameter is preferably at least 0.1, 0.3 or 0.5 μm, and in some instances can be at least 0.6 or 0.7 μm.

(a(ii)) Conductive Particles

Suitable conductive materials are those having electrical conductivity of at least $3.0 \times 10^7$ S/m at 20° C., such as silver, gold, copper, aluminium, and their alloys. Non-magnetic, conductive materials are detectable to an extent (particularly those conductive particles having a conductivity above $3.0 \times 10^7$ S/m at 20° C.) and may constitute a part or all of the metal detectable particles (a). In some embodiments, the conductive particles are free of high atomic mass elements.

The conductive particles are typically dense particles. The density is typically within the range of 2.0 to 23.0 g/cm$^3$, preferably between 2.5 to 20.0 g/cm$^3$.

The average particle size of particles (a(ii)) is suitably less than 30 μm, or less than 20 μm, or less than 15 μm. A suitable mass median diameter (D50) is within the range of 0.5-12 μm. The particle size is significant—if the particles are too small, the particles tend to aggregate, which is not desired in the present case as a dispersion throughout the film layer is desired, to retain physical properties of the film and detectability of the article or any portion thereof (above a minimum detectable volume). The particle size should also not be too large to avoid deterioration of film strength apart from rapid particle settling in the film-forming composition. The mass mean diameter is preferably not more than 1.8, 1.6, 1.4 or 1.2 μm. The mass mean diameter is preferably at least 0.1, 0.3 or 0.5 μm, and in some instances can be at least 0.6 or 0.7 μm.

(b) Particles Containing One or More High Atomic Mass Elements

The high atomic mass elements are those elements with an atomic mass of at least 132, covering caesium (atomic mass 132.91) and higher atomic mass elements. This encompasses the period 6 elements (being those elements within the sixth row or period of the periodic table). Typically, the high atomic mass element or elements of the particles of type (b) will be selected from the non-gaseous and non-radioactive high atomic mass elements. This class excludes elements such as radon (a noble gas) and polonium, and also the period 7 elements which are radioactive or in gaseous form. Of the elements, those with atomic numbers between 55 and 83, from caesium to bismuth, contain the most suitable examples. The element is suitably selected from one or more of caesium, barium, lanthanum, cerium, praseodymium, neodymium, samarium, europium, gadolinium, terbium, dysprosium, holmium, erbium, thulium, ytterbium, lutetium, hafnium, tantalum, tungsten, osmium, iridium, *aurum*, and bismuth. The oxides, carbides, sulfides, sulfates, ferrites, carbonates, hydroxides, halides, tellurides, titanates, tungstates and vanadates of these elements can be used. Combinations of one or more of the elements, or one or more of the compounds of the elements, may be used. Notable examples of materials fitting the description are barium compounds such as barium sulfate, lithopone and/or barium ferrite, bismuth compounds such as bismuth trioxide, bismuth oxychloride and/or bismuth vanadate, and tungsten metal or tungsten compounds such as tungsten trioxide, tungsten disulfide and/or tungsten carbide.

The particles (b) are suitably dense particles. The density of the particles (b) may be between 4.0-23.0 g/cm$^3$. The density of the particles (b) may be at least 7.0 g/cm$^3$, at least 10.0 g/cm$^3$, at least 13.0 g/cm$^3$ or least 15.0 g/cm$^3$, and is preferably at most 22.0, 21.0 or 20.0 g/cm$^3$. Any upper and lower limit may be combined to form a range. To achieve a suitable balance of properties in the glove (in terms of detectability, dispersion and suspension), the range may suitably be 7.0-20.0 g/cm$^3$, or between 15.0-21.0 g/cm$^3$.

The particle size of the particles (b) is suitably selected for incorporation into the film. The average particle size of particles (b) is suitably less than 20 μm. The average particle size (based on a mass mean diameter—D50) is preferably <20 μm, <15 μm, <10 μm, and may in some embodiments be less than 5 µm. The average particle size based on a mass mean diameter may be at least 0.1, 0.3, 0.5 or at least 1.0 µm. Any upper and lower limit may be combined to form a suitable target range for the particle size of the particles (b). A suitable mass median diameter (D50) providing a good balance of properties is within the range of 0.5-15 µm, such as 1-5 µm. The applicant has found that if the D50 is too low, there is clumping of the particles, even when other steps are taken to attempt to minimise clumping. This has a significant impact on the physical properties as well as overall minimum detectability limits of the product.

(It is noted that while it is possible for there to be some high atomic mass elements in the metallic particles or the conductive particles that may be present in the articles of the invention, for the purposes of this application they are not classified as "high atomic mass element particles" since their predominant characteristic is their magnetic or conductive properties. The amount of high atomic mass alloying elements may be up to 80% by weight of the magnetic or conductive particles. Provided that the particles have magnetic properties (a(i)), or conductive properties (a(ii)), then the particles will be considered constitute particles of types (a(i)) or (a(ii)), respectively.

It is also noted at this juncture that a "type" of particles refers to a volume or body of particles that are characterised by a particular chemical composition and having a predominant function (i.e. metal detectability function, or x-ray detectability function) in the article. Where two or more types are referred to, this means that the two volumes of particles can be characterised as being different to each other, in terms of their chemical composition. In some embodiments there are at least two types of particles, with one particle type providing metal detector detectability, and the other particle type providing x-ray detectability.

Coating or Encapsulation of Particles

A protective layer of a corrosion inhibitor can be provided onto the surface of particle (a(i)), or on particles (a(ii)) or (b), depending on the particular embodiment of the invention. The corrosion inhibitor may encapsulate the particles or be coated around the exterior. The shape of the particles (the particle core) can be spherical, rod-like, platelet-like or irregular.

By way of background, corrosion of particular types of particles (those based on metals) can be caused by either (1) oxidation (i.e. general corrosion), (2) chemical exposure to corrosive agents (e.g. by chlorine or sulphur), or (3) by exposure to acid or basic substances in end-use applications (e.g. foodstuffs that are acidic or basic that come into contact with the articles containing the particles—such as gloves). Corrosion of types (1) and (2) are particularly relevant to the presence of the corrodible particles that make up particles (a(i)), (a(ii)) and/or (b) in the elastomeric film-forming composition used to make the articles. Such compositions that are used for dip-forming gloves are based on aqueous suspensions of an elastomeric polymer ("latex") contain substances including water, chlorine and/or sulphur that can cause corrosion of the particles, and discolouration as a consequence.

A corrosion inhibitor is defined by ISO 8044 as 'a chemical substance that decreases the corrosion rate when present in the corrosion system (i.e. in the latex composition or in the final film) at suitable concentration, without significantly changing the concentration of any other corrosion agent'. The corrosion inhibitor forms a non-reactive (inert) layer on the surface of the metal particle to provide oxidation resistance, or corrosion resistance (in the environment in which it is present). The agent resists chemical/electrochemical reactions on the surface of the particles, thus at least slowing down (or mitigating) the corrosion process. The corrosion inhibition should be sufficient such that there are no visible signs of corrosion of the particles in the product by the end of the shelf-life of the product. Elastomeric articles have a shelf-life because, over time, the elastomeric properties deteriorate. The shelf-life may typically be about three to five years.

Types of Corrosion Inhibitors

The types of corrosion inhibitors (substances) that can be used in embodiments of the present invention include:

silicones such as polydimethylsiloxane and a silicon dioxides, waxes, such as paraffin wax, microcrystalline wax, carnauba wax and mineral wax, polymers such as acrylic polymer, vinyl polymer and epoxy (the polymers are preferably other than the main elastomeric polymers that form the elastomeric film, and the polymer forms of corrosion-inhibitors are preferably non-elastomeric polymers), corrosion-resistant metal salts (known as conversion coatings in some fields), such as metal phosphates (such as iron phosphate, manganese phosphate and zinc dihydrogen phosphate), metal borates and/or metal tungstates, and metal-based coatings based on corrosion-resistant metals such as stainless steel, chrome, zinc and aluminium—i.e. corrosion-resistant metal coating.

A combination of one or more of the above corrosion inhibitors may be used, within the same class or across different classes.

A subclass of corrosion inhibitors are the hydrophobic corrosion inhibitors. Such materials provide corrosion inhibition through creating a hydrophobic coating around the particles that repels water, to protect the core particles from corrosion caused by water. Examples include hydrophobic polymers, waxes and silicones.

Methods of Application (or Formation) of Corrosion Inhibitor Coating

The particles can be subjected to a process to prepare a corrosion inhibitor coating on the particles prior to preparation of the elastomeric articles (i.e. prior to formation of the elastomeric film-forming composition), or the coating can be prepared in situ (i.e. formed in the elastomeric film-forming composition, which then forms the film layer). Methods for the preparation of the coated particles in advance of the process for the formation of the elastomeric film include:

(i) Applying the coating material directly onto the particles by spraying or wet grinding, or a combination of both;

(ii) Mixing the coating material into a mixture of particles and solvent; or (iii) Chemically reacting the particles to be coated with a reagent that results in the conversion of particle composition at the surface of the particles into a corrosion inhibiting material (i.e. conversion coating).

Pre-treating the particles with an adhesion promoter (explained below) can be performed prior to step (i) and/or step (ii).

In all methods above, other processes to assist the dispersion of the particles and prevent aggregation may be employed, for example sonication.

Technique (iii) outlined above involves chemically reacting the surface of the particle with a suitable reagent, such as an acid that forms the desired conversion coating when reacted with the metal. This is normally done in the process of conversion coating, where a layer of corrosion inhibitor is chemically formed or deposited on the surface of the metal particle. Examples of suitable corrosion inhibitor coating materials that may be formed by a process of conversion coating are oxides such as iron oxides, chromates, phosphates, aluminate, oxalate, zirconate, and molybdates. In such cases, the particle core typically comprises a metal or combination of metals in the metallic state. Thus, conversion coating techniques are only suited to some classes of particles.

Function of Corrosion Inhibiting Layer

The corrosion inhibitor coating, or layer, allows metallic particles to be incorporated into water-based systems (e.g. water-based elastomeric film-forming compositions) without being susceptible to oxidation. This enables the production of metal detectable gloves containing pure metal particles or their alloys with better magnetization strength or high atomic weight elements, without concern for corrosion of those metals/alloys, thus producing enhanced detectability. This in turn enables the amount of particles (by wt % or phr) to be reduced, while still achieving sufficient detectability levels in small volumes of the elastomeric film.

Figure 6:
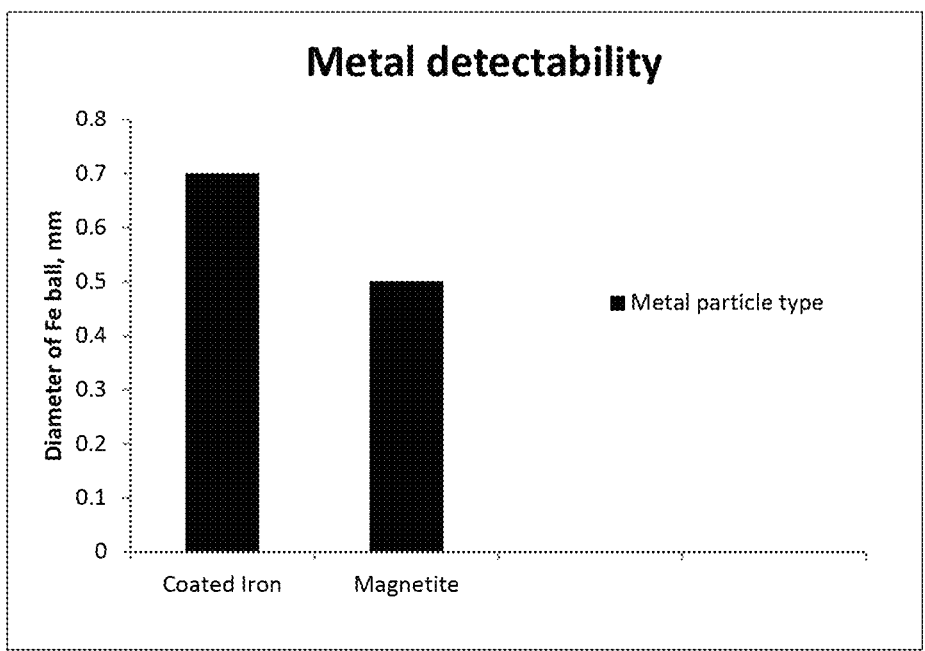
FIG. 6 is graph showing the metal detectability (y-axis) of two particulate materials (x-axis), measured by reference to the equivalent iron ball particle size that is equally as detectable as that particulate material. The particulate materials, from left to right, are coated iron particles and magnetite particles.

The applicant has conducted tests to compare the performance of iron-based particles, in either a coated or uncoated form. For the uncoated form of iron, magnetite (iron oxide) was used, as this material is of itself corrosion resistant (the corrodibility of iron prevents its use in uncoated form). For the coated form of the particle, iron metal was used, and was coated with a silane adhesion promoter followed by a coating of paraffin wax. The metal detection strength (detectability with metal detector) was tested for each material. For the same particle weight, the detection strength was higher for the iron metal with coating, than for magnetite (uncoated). This is shown in FIG. 6. The test for detectability is based on comparing the detection strength of the particular particles as compared to an iron ball of a particular diameter—the larger the equivalent diameter of the iron ball, the higher the detectability. The metal detectability of the coated iron particles was equivalent to an iron ball having a diameter of 0.7 mm, compared to 0.5 mm for uncoated iron oxide. This modification therefore enables the use of a smaller amount of metal particles in the article, based on a more detectable substance (e.g. iron metal), with the aid of a corrosion inhibiting coating. This allows for gloves to be fully produced in various colours. The coating may be a pigmented layer, and may provide the associated colour hue to the article (glove). Otherwise, the article such as a glove may have a metallic lustre from the metal particle.

Functional Layer—Adhesion Promoter

Figure 5:
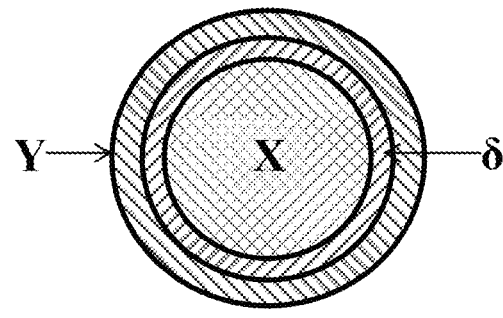
FIG. 5 a schematic illustration of coated magnetic particles in accordance with an embodiment of one of the inventions described herein.

The particles may further comprise a functional layer, which may be an adhesion promoter, between the particle core (type (a(i)), (a(ii)) or (b)), and the coating. This is illustrated schematically in FIG. 5, where X represents the core (of type (a(i)), (a(ii)) or (b)), δ represents the adhesion promoter, and Y represents the corrosion inhibitor coating.

An adhesion promoter is a material that promotes or aids adhesion of the coating to the particle core. The adhesion promoter may be a chemical substance comprising bifunctional groups.

These groups allow adhesion or reaction to the particle core material, and the coating material. The layer may alternatively be described as a pre-treatment layer that is able to react and form chemical bonds with the inorganic core material, and the coating, which may be an organic coating (e.g. an organic polymer). The adhesion promoter is particularly suited to organic coatings, and acts at the interface between the inorganic core (such as iron or aluminium) and the coating (e.g. acrylic), to enhance adhesion between the two. This is an optional layer.

Examples of adhesion promoters include peroxides such as dicumyl peroxide, diamines such as 4,4'-diaminodiphenylmethane, bi-functional copolymers such as polypropylene-grafted acrylic acid, silane coupling agents having functional groups which include epoxy groups, amino groups, vinyl groups, mercapto groups, and methacryloxyl groups (example of silane couping agent is 3-aminopropyltriethoxysilane and 3-(2,3-epoxypropoxy)propyltrimethoxysilane; titanate coupling agents such as neoalkoxy titanate, zirconate coupling agents such as neoalkoxy zirconate; and aluminate coupling agents such as alkylacetoacetate aluminum di-isopropylate as non-exhaustive examples.

The relative amount of corrosion inhibitor coating to particle core may be between 5 and 50% by weight. The amount of corrosion inhibitor coating may optionally be within the range of 10-35% by weight, or about 10-15% by weight, based on the total particle weight. The amount is more readily determined for coating techniques that involve the addition of a coating layer to the particles. In the case of conversion coatings, or the formation of the coating layer in situ, it may be more difficult to determine the relative amounts. Nevertheless, for such coating techniques, the coating is sufficient to surround the cores and to produce an effective corrosion resistant coating around the particles.

Amounts of Particles

The relative amount or ratio of particles (a) to particles (b) may broadly be between 1:99 and 99:1. The ratio of particles (a) to particles (b) is preferably between 10:90 and 90:10. In some embodiments, the ratio of particles (a) to particles (b) is between 50:50 and 90:10. These ratios apply regardless of whether (a) refers to (a(i)) particles only, (a(ii)) particles, only, or a combination of particles (a(i)) and (a(ii)). Where particles (a(i)) and (a(ii)) are both present, the relative amount of those particles is between 10:90 to 90:10. When all three particle types are incorporated together, the relative amount or ratio of particles (a(i)) to particles (a(ii)) to particles (b), may broadly be between 1:1:98, 1:98:1 and 98:1:1, or between 10:10:80, 10:80:10 and 80:10:10. In some embodiments, the ratio of particles (a) to particles (b) and (c) is 30:20:50. Where the particles are coated particles of type (a(i)), these particles may be present without the incorporation of particles (a(i)) and (b).

The total amount of particles may broadly be in the range of 2% and 80% by weight of the article. In particular embodiments, the amount is a minimum of at least 2%, 3%, 4%, 5%, 6%, 7%, 8%, 9% or 10% by weight of the article. For metal detection only, a glove having 0.05% by weight of particles (a) is detectable, while x-ray detection of the glove is enhanced when using at least (about) 2.0% by weight of particles (b). For this reason, the preferred total amount of particles (a) and (b) is at least about 2.0% by weight. To achieve the best film properties, the amount is suitably not more than 60%, 50%, 40% or 30% by weight of the article. Any minimum and maximum may be combined without limitation to form a range. It is notable that where the amount is around 5% to 40% or 5% to 30%, or 10%-30% by weight of the article, a good balance is achieved between the film properties (i.e. the amount is not so high as to deteriorate the film properties to such a degree that the articles such as gloves are not considered commercially acceptable to the market), but due to the balance of particle types, the required minimum detectability desired for the articles (such that small pieces can be detected) is achieved. This range is particularly suited to products having a thickness between 0.05-3 mm, such as between 0.05-2 mm, and suitably between 0.05 and 1 mm, although products of thicknesses outside this range are also encompassed by the present application.

The amount of particles (a(i)), (a(ii)) and/or (b) may alternatively be calculated by reference to the parts of rubber/elastomer in the product (per hundred parts of the rubber/elastomer). The total amount of particles in some embodiments may be between 2-100 phr. For metal detection only, the amount of particles (a) may be a minimum of 0.05 phr to produce metal-detectable product, while for x-ray detection, the amount of particles (b) is preferably at least 2.0 phr for enhanced x-ray detection. In total, the amount of particles (a) and (b) should be least (about) 2.0 phr for multi-detectability. The minimum amount may be at least 5 or at least 10 phr, and the maximum amount may be not more than 50 phr, not more than 40 phr, or not more than 20 phr. Suitable ranges include 5-40 phr and 10-20 phr, to provide a suitable balance between detectability, good suspension in the film-forming composition, and good maintenance of elastomeric film properties.

The total amount of particles (a) and (b) will impact on the minimum detectability (minimum detectable volume) of a portion of the article. The applicant has conducted tests to determine what minimum detectability they can achieve with the articles of the present application. The applicant produced a glove containing 80% by weight of a combination of particles (a) and (b) (those particles being present in a 90:10 ratio). The product was able to be detected at a volume of 0.08 $mm^3$ using metal detection, and 0.05 $mm^3$ by x-ray detection. Metal detection in this test was set at a detection sensitivity of iron (Fe) having 0.5 mm diameter. X-ray detection was carried out by testing against 0.12 mm-thick aluminium foil as the detection baseline. Accordingly, this test work demonstrated that detectability at 0.1 $mm^3$ is achievable with the concept of the present application. For products containing lower volumes of particles, good target minimum detectabilities may be higher than this, and be extremely commercially useful. Thus, in some embodiments, the product is detectable by both metal detection and x-ray detection (above a 0.12 mm thick aluminium film) at sample volumes of 0.2, 0.3, 0.4, 0.5, 0.6, 0.7, 0.8, 0.9 or 1.0 $mm^3$ in size.

FIGS. 1(A), 1(B), 1(C), 1(D), 1(E), 1(F), 1(G) and 1(H) illustrate some alternative arrangements for the distribution of particles for the production of multi-detectable articles having particles (a) (which may be of type (a(i) and/or (a(ii))) and (b). The particles (a) and (b) may be present in separate film layers, where the article comprises more than one film layer, as illustrated in FIGS. 1(F) and 1(G). The particles are distributed uniformly throughout the film layer in which they are present. In the case of FIG. 1(G), there is also a film layer that is free of each of particles (a) and (b).

The particles (a(i)), (a(ii)) and (b) may be in combination and are dispersed uniformly throughout at least one film layer. This may be the sole film layer of a single-layer elastomeric film article (FIG. 1(E)). Alternatively, the particles (a) (which may be (a(i)) and/or (a(ii)) particles) and (b) may be uniformly distributed throughout each film layer or all film layers of the elastomeric article. This is illustrated in FIG. 1(A).

In other embodiments, the particles (a) and (b) may be in combination and uniformly distributed in two more layers of a multilayer film. There may in this case be additional layers of the film that are free of the particles (a) and (b). Three such arrangements are illustrated in FIGS. 1(B), 1(C), and 1(D). In FIG. 1(B), the particles are within two layers and an external film layer of the multilayered film is free of the particles, in FIG. 1(C), both external film layers are free of the particles (a) and (b), and in FIG. 1(D), there are alternating particle-free and particle-containing film layers. An advantage of arrangements shown in FIGS. 1(B) and 1(C) is that the particle-free layers may be pigmented, and this arrangement, combined with the choice and loading of the particles (a) and (b) can enable coloured articles to be produced that do not have a grey appearance that might otherwise be associated with elastomeric articles containing iron-based particles. The pigments and arrangements described herein allow for the production of articles, such as gloves, of any intended colour.

For embodiments based on coated particles of type (a(i)) only, or based on one particle type only (e.g. coated or uncoated magnetic particles, with a pseudoplastic viscosity modifier), the same arrangements and amounts may apply but with the removal of the particles of type (b). The amount of particles a(i) may be between about 2 and 80% by weight of the article, preferably between 2 and 50% by weight, between 2 and 40%, 2 and 30%, 2 and 20% by weight, or between 5 and 50%, 5 and 40%, 5 and 30% or 5 and 20% by weight of the article, or between 10 and 50%, 10 and 40%, 10 and 30% by weight of the article. If all three types of particles are present (whether or not those particles are coated or uncoated), the particles of types (a(i)) and (a(ii)) may be present in the same layer in combination, or they could be present in separate layers. One of those particle types could be combined with particles of type (b). All permutations are possible.

The particles are suitably well dispersed in the elastomeric film-forming composition. This applies in particular to the composition at the time of production of the articles, to ensure uniform distribution in the film layer. The particles should not be in the form of aggregates (noting that aggregates involve strongly bonded clusters of particles that are difficult to disaggregate). In some embodiments of the invention, this is achieved by using a pseudoplastic viscosity modifier to disperse the particles throughout the elastomeric film-forming composition. This viscosity modifier is very effective in maintaining the dispersion of the particles for long enough for the final product produced from the composition to maintain well-dispersed non-aggregated particles. The particles can be coated and surface treated. The particles are uniformly distributed in the film layer(s) in which they are present.

Elastomers

The elastomeric film-forming composition comprises an elastomer-forming polymer (or polymer for short), in suspension or emulsion form. The polymer may be natural rubber or a synthetic polymer. The polymer is one that can be cross-linked to produce an elastomeric film. The polymer may be a single polymer or a combination (blend) of two or more polymers. The or each polymer may be a homopolymer or a copolymer, a grafted or modified polymer, or a blend thereof.

The polymer may contain free ionically cross-linkable groups, covalently cross-linkable groups, or a combination of both. Examples of ionically cross-linkable groups are acids, including carboxylates, sulfonates and acid anhydrides, and an example of a covalently cross-linkable group is a double bond.

The polymers may be selected from rubber (natural or synthetic), nitrile rubber, polyurethane, silicone rubber, polyisoprene, polychloroprene, acrylic polymers (including acrylic diene block copolymers), styrene-butadiene, polybutadienes, copolymers of these and other polymers/monomers (random copolymers, block copolymers or otherwise)

and modified forms of these polymers or copolymers (e.g. polymers containing additional substituents such as carboxylate, sulfonate, halide or other substituents) and thermoplastic elastomers. Examples of suitable thermoplastic elastomers include block copolymers such as styrene-butadiene-styrene, styrene-isoprene-styrene, styrene-ethylene-butadiene-styrene; thermoplastic polyurethanes and thermoplastic polyamides; thermoplastic vulcanizates such as vulcanized PP/EPDM compound; copolyester elastomers; metallocene-catalyzed polyolefin elastomers such as very low molecular weight, linear low density polyethylenes (VLMW-LLDPE); and reactor-made thermoplastic polyolefin elastomers. The articles are generally PVC-free articles.

One class of polymer that may be used is that obtained by copolymerisation of conjugated diene monomers and ethylenically unsaturated acid monomers (carboxylated polyacrylonitrile butadiene being an example of such a copolymer), synthetic polyisoprene, polychloroprene, styrene copolymers and/or polyurethane. Amongst the range of conjugated diene monomers, examples are 1,3-butadiene, iso-prene, 2,3-dimethyl-1,3-butadiene, 2-ethyl-1,3-butadiene, 1,3-pentadiene, chloroprene and acrylonitrile. Regarding ethylenically unsaturated acid monomers, the acid group may be a carboxyl group, a sulfonic acid group or an acid anhydride group. Examples of ethylenically unsaturated acid monomers include acrylic acid or methacrylic acid; itaconic acid, maleic acid, fumaric acid, maleic anhydride, citraconic anhydride, sytrenesulfonic acid, monobutyl fumarate, monobutyl maleate, mono-2-hydroxypropyl maleate, and alkali metal or ammonium salts thereof. The polymers used may be carboxylated or non-carboxylated, as desired.

One notable example of a suitable polymer is polyacrylonitrile butadiene. This may be carboxylated or non-carboxylated. This may be provided as a mixture of carboxylated nitrile latex and nitrile butadiene rubber.

Carboxylated refers to the presence of carboxylate (carboxylic acid or ester) groups on the polymer chain. Carboxylation may be achieved by forming the polymer with a monomer containing carboxylate groups, or through grafting carboxylate groups to a polymer. As examples of suitable carboxylated polymers, reference is made to PCT/AU2014/000726 and PCT/AU2014/000727, the entirety of each being incorporated into this specification by reference. The carboxylation degree may be between 5-15%, or between 5-10%.

When producing the gloves using a dipping process, the polymer is provided initially in the form of an aqueous suspension. The aqueous suspension suitably has a pH of at least 9.0. The elastomeric film-forming composition can also be referred to as the "synthetic latex composition" or "latex composition". It is common in the art to use the expression "latex" or "rubber" to refer to any polymer in a general sense, and "latex composition" is used in a corresponding manner. Latex is not to be read as referring to natural rubber latex.

In the art of the present invention, it is common to refer to the amount of the elastomer-forming polymer as being 100 phr (per hundred parts "rubber"), and for the relative amounts of the remaining components of a composition for producing an elastomeric film to be calculated as a number of parts compared to the 100 phr of the elastomer-forming polymer, by weight. Thus, for an amount of cross-linking agent that is 1/100th that of the elastomer-forming polymer in the composition by weight, the amount of cross-linking agent is referred to as 1.0 phr.

Other Components Used to Produce the Elastomeric Articles

The elastomer-forming polymers are cross-linked with one or more cross-linking agents to produce the elastomeric film. Various types of cross-linking agents can be used. Other agents that may be present in the composition used to produce the elastomeric film-forming composition include viscosity modifiers, softeners, anti-ozonants, stabilizers such as pH stabilizers, surfactants, emulsifiers, antioxidants, vulcanizing agents, polymerization initiators, pigments, fillers, colorizing agents and sensitizers. Many of these agents are added in particulate form. Others are added as liquids. These are added prior to forming the latex composition (i.e. elastomeric film-forming composition) into the shape of the synthetic elastomeric article. In some embodiments they are added at the same time as the cross-linking agent. In other embodiments, they are added after.

One significant component of the elastomeric film-forming composition that addresses the high loading of particulate materials without settling is a viscosity modifier. This is described in further detail below.

Cross-Linking Agents

Cross-linking agent classes include ionic cross-linking agents and covalent cross-linking agents. The cross-linking agent or agents used in the production of the elastomeric gloves may be selected from ionic cross-linking agents, covalent cross-linking agents, and combinations thereof.

Ionic cross-linking agents include multivalent metal-based cross-linking agents. Examples of ionic cross-linking agents include multivalent metal oxide cross linking agents (such as zinc oxide and magnesium oxide), peroxides (such as 1,1-di(t-butylperoxy)-3,3,5-trimethylcyclohexane, which can be purchased under the trade name Trigonox 29-40B-pd) and solubilized ionic cross-linking agents such as multimetal oxides of multivalent metals (e.g. sodium aluminate), multivalent metal hydroxides, and multivalent metal salts—particularly the solubilized trivalent metal-based cross-linking agents. Other ionic cross-linking agents amongst those known in the art and be used. These include the cross-linking agents described in PCT/AU2016/050308, PCT/AU2016/050311 and PCT/AU2016/050312, the entirety of each being incorporated by reference.

Covalent cross-linking agents include organic cross-linking agents, sulphur and/or sulphur donors, and combinations thereof.

Sulphur may be added in the form of elemental sulphur. Sulphur may be added in the form of a sulphur donor. Examples of suitable sulphur donors include the carbamates such as thiocarbamates (e.g. zinc dibutyl dithiocarbamate (ZDBC), Zinc diethyl dithiocarbamate (ZDEC); Zinc dimethyl dithiocarbamate (ZDMC); thiurams (eg. tetraethylthiuram disulfide (TETD), Tetramethylthiuram disulphide (TMTD)); Dipentamethylene thiuram tetrasulfide (DPTT); Dipentamethylene thiuram hexasulfide (DPTH); Dipentamethylene thiuram hexasulfide; thiourea (Ethyl thiourea (ETU) and diphenylthiourea (DPTU); thiazoles (e.g. Mercapto Benzothiazoles (MBT), Mercapto Benzothiozole disulphide (MBTS), zinc 2-mercaptobenzothiazole (ZMBT)); guanidines (eg. Diphenylguanidine (DPG)) and aldehyde/amine-based sulphur donors (eg. hexamethylenetetramine). Other examples are well known in the art and can be obtained from various publicly available sources.

Other cross-linking agents that may be used can be selected from crosslinking monomers, reactive oligomers, polyisocyanate oligomers, functional crosslinkable polymers, derivatives of ethylene glycol di(meth)acrylate (such as ethylene glycol diacrylate, di(ethylene glycol) diacrylate, tetra(methylene/ethylene glycol) diacrylate, ethylene glycol dimethacrylate (EDMA), di(ethylene glycol) dimethacrylate (DEDMA), tri(methylene/ethylene glycol) dimethacrylate, tetraethylene glycol dimethacrlate (TEDMA)), derivatives of methylenebisacrylamide (such as N,N.-methylenebisacrylamide, N,N.-methylenebisacrylamide, N,N.-(1,2 dihydroxyethylene)bisacrylamide), formaldehyde-free cross-linking agents (such as N-(1-Hydroxy-2,2-dimethoxyethyl) acrylamide), divinylbenzene, divinylether, diallyl phthalate, divinylsulfone, Trimethylolpropane Trimethacrylate (TMPTMA), polyfunctional cross-linkers and the like. Combinations of these cross-linking agents can also be used.

In broad terms, any amount of cross-linker may be used, as required for the final article properties. Thus, the total amount of cross-linking agents in the composition may be between 0.01 and 14 phr. However, it is usually desirable to minimise cross-linker amounts (and the associated costs or disadvantages). The total cross-linking agent amount may be within one of the following ranges: 0.01-14.5 phr, 0.2-12.5 phr, 0.3-10 phr, 0.1-10 phr, 0.2-10 phr, 0.3-9 phr, 0.5-9 phr, 0.8-9 phr, 0.3-8 phr, 0.5-8 phr, 0.8-6 phr, 1-5 phr, 2-9 phr, 3-10 phr, 3-7 phr, 1-3 phr, 0.01-0.5 phr, 0.01-1.0 phr.

The amount of ionic cross-linking agent may be between 0.0-6.0 phr, such as 0.01-6.0, or 0.01-5.0 phr. The amount is preferably lower still, at 0.01-3.0 phr, or 0.01-2.0 phr, 0.01-1.0 phr, 0.01-0.7 phr, 0.01-0.6 phr or 0.01-0.5 phr.

The amount of sulphur may be between 0.0-5.5 phr. The amount may be lower still, at 0.0-3.5 phr, such as 0.01-3.0 phr, 0.01-2.0 phr, 0.01-1.5 phr, 0.01-1.0 phr, 0.01-0.7 phr, 0.01-0.5 phr or 0.01-0.3 phr.

The amount of sulphur donor may be between 0.0-2.0 phr, such as between 0.01-1.5 phr, 0.01-1.0 phr, 0.2-1.0 phr, 0.01-0.7 phr, 0.01-0.5 phr, 0.01-0.3 phr, 0.05-0.2 phr, 0.3-2.0 phr, 0.3-1.5 phr or 0.2-0.6 phr.

The amount of organic cross-linking agent may be between 0.0-4.0 phr, such as 0.01-4.0. The amount may be lower still, at 0.01-3.0 phr, or 0.01-2.0 phr, or 0.01-1.0 phr.

The cross-linking agent can be combined with the latex composition and other components of the elastomeric film-forming composition at suitable time points for the formation of the desired type of film. Cross-linking agents are typically added to the latex composition with other components, however for some forms of cross-linking agent (such as the solubilised ionic cross-linking agents, including sodium aluminate) there is a preliminary step involving the formation of a cross-linking composition and combining this with the latex under controlled conditions, followed by the addition of other components and secondary cross-linking agents.

Cross-linking Composition

In some embodiments, a cross-linking composition comprising a trivalent metal-based cross-linking agent is used. This is suitably in the form of a formulation comprising (i) a solution of a trivalent metal source, combined with (ii) a strong hydroxide (e.g. sodium hydroxide, potassium hydroxide, ammonium hydroxide, or a combination thereof), and optionally (iii) a mechanical stabiliser, having a pH of at least 9.0. This cross-linking composition is as described in any of PCT/AU2016/050308, PCT/AU2016/050311 and PCT/AU2016/050312, referred to above. The trivalent metal is preferably aluminium, although this may be interchanged with any of the sources described in the referenced PCT applications. The selection of this cross-linking agent, in a formulation providing around 0.1-0.5 phr of the trivalent metal source (e.g. sodium aluminate, aluminium hydroxide, or soluble aluminium salt), allows for the formation of a film of suitable properties, even when high loadings of particles (a) and (b). The results presented herein show the notable improvements in film properties using this selection of cross-linking agent, compared to a comparative formulation without this reagent. The amount of strong hydroxide is suitably between 0.01-5 phr, usually within a ratio of between 2:1-1:2 (based on phr) with respect to the trivalent metal source. Thus, the amount may be between 0.05-1.0 phr in some embodiments. In addition to influencing the pH of the cross-linking composition, the strong hydroxide within this cross-linking composition has an influence on the stability of the complex ions formed from the trivalent metal source in solution, and on the activation of the trivalent metal. The mechanic stabiliser in this composition may be a water-miscible or water-soluble organic polyol, or a water-soluble or water-miscible thickening agent, examples of which are well known in food or pharmaceutical manufacture. The amount of this agent may also be between 0.01-5 phr, and in some embodiments is within a ratio of between 2:1-1:2 (based on phr) with respect to the trivalent metal source. The amount may for example be between 0.05-1.0 phr, or 0.05-4.0 phr, 0.05-3.0 phr, 0.05-2.0 phr, 0.1-2.0 phr, 0.5-3.0 phr, 0.5-2.0 phr or 0.1-1.0 phr. Examples of such polyols and thickeners include glycerine, sugars and sugar alcohols, maltodextrin, polysaccharide, polyglycerol, starch, modified starch, and mixtures thereof.

Initially, when such a cross-linking composition is used as the (or one of the) cross-linkers, a relatively highly concentrated cross-linking composition is prepared, and then this is diluted prior to use. Relative amounts of components used in the production of the concentrated cross-linking composition may be, per 100 parts by weight of water:

Between 0.01 and 5 parts of the trivalent metal source; and

Between 0.01 and 5 parts of strong hydroxide (preferably between 0.05 and 4 parts when using component (a) above, between 0.05 and 3 parts when using component (b) above, or between 0.05 and 4 parts when using component (c) above), and optionally Between 0.03 and 15 parts of mechanical stabiliser (i.e. total stabiliser, in the case of a mixture; preferably between 0.5 and 3 parts).

The dilution is usually performed to reduce the concentration such that the trivalent metal ion concentration is reduced to between 0.33-3.3% by weight of the cross-linking composition. The amount used phr of rubber is usually between 0.01 and 0.5 phr, based on the trivalent metal source (with 0.01-0.5 phr of the strong hydroxide, and 0.03-1.5 phr of the stabiliser).

Other Components of the Elastomeric Article-Forming Composition

A preferred component of the composition is a viscosity modifier.

The dense, heavy particles (a) and (b) have a tendency to settle within the elastomeric article-forming composition. The same applies for coated magnetic particles, or uncoated particles of types (a) or (b), which are also typically dense and heavy. Having considered and tested a number of options, it was found that a viscosity modifier could be used to suspend the particles and stabilize the dispersion of particles. There was uncertainty as to whether a viscosity modifier would be effective in suspending the particles effectively, especially given the weight of the particles, and whether the increase in viscosity would adversely impact on the ability to form a film from the composition of the required thickness suitable for producing thin film articles such as gloves. There was also uncertainty about the flow properties of the composition, which might have adversely impacted on the mechanics of operating a dipped article production line. Another potential problem was the potential entrapment of air within the film-forming composition, which would create bubbles on the surface of the composition during dipping.

Bubbles are problematic, as bubbles in a film layer creates an area of weakness or a pin-hole in the article, which cannot be accepted for thin film barrier products such as gloves.

Ultimately, it was found that by using a viscosity modifier that imparts pseudoplastic characteristics (i.e. a pseudoplastic viscosity modifier), a balance could be achieved between suspension of the particles, while avoiding excessively high viscosity and bubble entrapment. The pseudoplastic characteristics allow for the viscosity to be reduced through increasing shear, through stirring. Wth increased agitation (stirring) of the composition, the viscosity can be reduced by at least 25%. In some cases, the pseudoplastic viscosity modifier can result in a viscosity reduction of around 50% (e.g. within the range of between 25% and 70% viscosity reduction, or between 30% and 70% viscosity reduction, measured in centipoise), which assists in releasing the trapped air. The combination of viscosity modifier and stirring achieves acceptable viscosity to suspend the particles, avoid air entrapment, and allow for good processing/production conditions, including good pumpability (i.e. ability to pump the composition from storage tanks into dipping tanks). Sonication can also be used to assist in the release of bubbles of trapped air, without causing settling of the particles.

In some embodiments where the use of a pseudoplastic viscosity modifier is not specifically required (e.g. for multi-detectable particles (a) and (b) together), the viscosity modifier may be a water-miscible or water-soluble organic polyol, or a water-soluble or water-miscible thickening agent, examples of which are well known in food or pharmaceutical manufacture. Naturally-sourced or derived viscosity modifiers include gums, casein, saccharides, cellulose thickeners, clays and the like. Synthetic viscosity modifiers include acrylic thickeners, alkali-swellable thickeners, wax thickeners and non-associative thickeners. Combinations of viscosity modifier types can also be used, such as ASE and polysaccharide. In embodiment of the invention, a non-associative thickener is used. Thickeners that provide Newtonian or shear-thickening properties to the composition, such as associative polyurethane thickeners, hydrophobically-modified polyether thickeners for Newtonion flow behavior, polyethylene glycol or propylene glycol should be avoided, as they do not provide the required properties.

In preferred embodiments, and in the aspects of the invention that relate to the use of a single type of particles (e.g. coated or uncoated magnetite) and a pseudoplastic viscosity modifier, the viscosity modifier must be one that imparts pseudoplastic properties to the latex mixture. Examples of pseudoplastic viscosity modifiers include non-associative alkali-swellable emulsion (ASE) type thickeners (e.g. acrylic alkali-swellable emulsion thickeners), polysaccharides such as xanthan gum, and fumed silica. Cellulosic thickeners can be used, but are less preferred. Silicates and activated phyllosilicates can be used, but these are less preferred. ASE thickeners are a known class of materials, based on a dispersion of acid-functional acrylic polymers in water. One example is Rheovis AS1125, but many others are available. (Hydrophobically-modified ASE thickeners, however, are preferably avoided.) The pseudoplastic properties can be measured by preparing a formulation (dip formulation containing latex, cross-linkers, particles, etc.) containing the selected viscosity modifier, measuring the viscosity (Brookfield viscometer, spindle no. 3, 30 rpm) after 24 hours, and comparing this to the viscosity measured at 60 rpm after 24 hours. If the viscosity is less at 60 rpm, then this indicates pseudoplastic properties. Preferably, the pseudoplastic properties are highly pseudoplastic properties. For example, it is desirable that stirring of the composition achieves at least a 25% reduction in the viscosity reading of the composition (at 60 rpm compared to 30 rpm), preferably at least a 30% or a 40% reduction in the viscosity reading of the composition.

The viscosity modifier is suitably used in an amount to provide a viscosity to the elastomeric film-forming composition of between 50 and 1200 centipoise (cps), when tested using a Brookfield viscometer, spindle no. 3, at 30 rpm, after 24 hours. Where testing with spindle 3 is not possible, spindle no. 1 or 2 can be used. For consistency of testing, the tests should be conducted at a temperature of 25° C. The most preferred viscosity ranges, are 100-300, 200-1200, 200-1000, 250-1000, 200-500, or 250-800, or 500-1000, based on the test results shown in Tables 19(a) to 20.

A range of values which are not desirable, according to Tables 19(a), 19(b) and 20 is below 50 cps and above 1600 cps. Nevertheless, it may be possible in some instances for the viscosity to be below 50 cps, and to rely on constant agitation to keep the particles in suspension and distributed throughout the composition during dipping, and to achieve a viable product.

The amount of viscosity modifier may be within the range of 0.1-10 phr, such as 0.5-10 phr or 0.5-6.0 phr, although this may vary depending on the choice of viscosity modifier, viscosity of the elastomeric film-forming composition without the modifier, the pH and temperature. The minimum amount is preferably at least 0.5, 0.75, 1.0, 1.25, 1.5, 1.75, 2.0, 2.25, 2.5 or 2.75 phr. The maximum amount may be 10, 9, 8, 7, 6 or 5 phr. These amounts suit acrylic thickeners, such as ASE-type thickeners, in particular. These amounts also suit polysaccharide thickeners.

The amounts may be approximately the same for other types of thickeners, and may be adjusted for those having a greater effect at lower concentrations (e.g. HASE-type thickeners).

In some embodiments, the viscosity modifier is leached out from the article during the later stages of article manufacture. For example, in a dipping process, the viscosity modifier may be leached out of the cured product during washing stages. There may nevertheless be some viscosity modifier that remains in the article product, indicative of its presence in the composition used to form the product.

Stabilisers may be used in the elastomeric film-forming composition. The stabilizer may be, for example, an anionic surfactant and or other non-ionic surfactants. The elastomer-forming polymer can be diluted with a solution of a stabilizer, such as potassium hydroxide, ammonium hydroxide and/or sodium hydroxide. The amount of stabiliser used is dependent on the polymer used in the elastomeric film-forming composition, the pH of the composition and other factors. The stabiliser can range from 0.1-5.0 phr, e.g. 0.5 to 2 phr, preferably 1.0 to 1.5 phr, which is diluted with water, preferably filtered water or de-ionized water, or water having a total solid content of around 5 ppm level.

Emulsifiers may be used in the elastomeric film-forming composition. Suitable emulsifiers include sodium alkyl aryl sulphates, sodium alkyl sulphates or other anionic/non-ionic surfactants. The amount of emulsifier used is dependent on the polymer used in the elastomeric film-forming composition, the pH of the composition and other factors. The amount of emulsifier can range from about 0.1 to 3 phr.

pH stabilisers may be used to avoid the possibility of destabilization, which is possible where the polymer contains carboxylic acid groups. Suitable pH stabilisers include potassium hydroxide, ammonium hydroxide and/or sodium hydroxide. Preferably, the pH stabiliser is potassium hydroxide. A diluted stabilizer solution can be mixed with the polymer. The pH of the mixture is suitably adjusted to between about 8.5 to about 12.5, or between about 8.5 to about 11.0. The cross-linking agent(s) can then be added to the mixture.

Antioxidants may be added to the elastomeric film-forming composition of the present invention. Suitable antioxidants include hindered arylamines or polymeric hindered phenols, and Wngstay L (the product of p-cresol and dicyclopentadiene). The antioxidant may, for example, be added in an amount ranging from 0.0-5.0 phr, 0.0-3.0 phr, 0.0-1.0 phr or 0.3-0.5 phr.

Pigments such as titanium dioxide, selected for its pigmentation, to reduce the transparency of the final elastomeric film, may be added in amounts ranging from 0.01-10.0 phr, such as 1.5-2.0 phr or 1.0-3.0 phr and colorants can also be added in the desired amounts. The mixture is then diluted to the target total solids concentration by the addition of a liquid, such as water. The pigments used in the elastomeric film-forming composition may be selected from the group consisting of EN/USFDA approved dyes.

Rubber reodorant may be used in the elastomeric film-forming composition. Suitable rubber reodorant include perfume oils of natural or synthetic origins. The amount of rubber reodorant can range from about 0.001 to 2.0 phr.

Wetting agents may be used in the elastomeric film-forming composition. Suitable wetting agent emulsifiers include anionic surfactants like sodium dodecyl benzene sulfonate or sodium lauryl ether sulfate, or non-ionic ethoxylated alkyl phenols such as octylphenoxy polyethoxy ethanol or other non-ionic wetting agents. The amount of wetting agent can range from about 0.001 to 2.0 phr.

Defoamers may be used in the elastomeric film-forming composition. Defoamers may be chosen from naphthalene type defoamers, silicone type defoamers and other non-hydrocarbon type defoamers or defoamers of refined oil of vegetable origin. The amount of defoamers can range from about 0.001 to 2.0 phr.

The elastomeric film-forming composition could also be blended with inorganic filler. Suitable inorganic fillers include titanium calcium carbonate, carbon black or clay. Preferably, the amount of inorganic filler included in the blend would not exceed 75% either alone or in combination. It will be appreciated that the blended composition will retain the favorable properties.

Sensitisers are chemicals that can be used in compositions for producing elastomeric films to control the amount of the composition that will remain coated on the mould during dipping (film deposition). Examples of sensitisers known in the art that can be used in the composition for producing an elastomeric film include polyvinyl methyl ether, polypropylene glycol, ammonium nitrate and ammonium chloride. The amount is generally between 0.01 to 2.0 phr, e.g. 0.1 to 1.0 phr. When other techniques are used for controlling the film thickness on the mould, such as the use of pre-dipping the mould into coagulant before undertaking the multiple dipping into the composition for producing the elastomeric film, the composition for producing an elastomeric film may not require a sensitiser.

Those skilled in the art will readily be able to vary the components of the elastomeric glove or film-forming composition to suit the circumstances. It will also be understood by those of skill in the art that specific chemicals or compounds which have been listed above are intended to be representative of conventional materials that may be used in formulating the elastomeric film-forming composition and are merely intended as non-limiting examples of each such component of the composition.

The elastomeric film-forming composition may be prepared by the following steps:

Solubilising any cross-linking agents that require solubilisation prior to adding to the latex composition;

Combining a dispersion of the elastomer with the cross-linking agents,

Adding particles (a(i)), (a(ii)) and/or (b),

Adding viscosity modifier, followed by

Stirring to homogenize the viscosity modifier throughout the composition and distribute particles (a(i)), (a(ii)) and/or (b) throughout the composition, and Diluting to reduce the total solids content for the formulation.

Particles (a(i)), (a(ii)) and/or (b) were preferably prepared beforehand in a liquid medium which may include ionic and/or non-ionic surfactants, dispersants and the like which function to prevent agglomeration or aggregation of the particles in said liquid medium. Other additives that may be added to improve stability of the dispersion are viscosity modifiers, anti-settling agents and humectants. Suitably the latex composition may also have such surfactants, dispersants and viscosity modifiers to prevent the agglomeration or aggregation of the particles in the composition. Examples of anti-settling agents include fumed silica, clay (e.g. organic clay) such as bentonite, polyamide, polyolefin particles and sulfonates. Examples of humectants include glycols such as propylene glycol, sugar polyols such as glycerine and other suitable hygroscopic additives.

The composition should be kept agitated for the duration of the time during which formers are dipped into the composition.

Preparation of Elastomeric Articles

The composition is formed into the shape of a glove, and then cured. Curing is used in a general sense, to refer to the stage during which cross-linking within the article is accomplished. Curing conditions are known to those skilled in the art.

Any known techniques can be used to form the desired shape of the elastomeric article, including dipping process, extrusion or otherwise.

A dipping process involves dipping a former into the composition, and curing the composition on the former. The cured product (the article) is then stripped from the former. Dipping is a particularly suitable process for glove and finger-cot manufacture.

The steps in the manufacture of the gloves using a dipping process are as generally described in PCT/AU2014/000726 and PCT/AU2014/000727. Those patent publications relate to the production of unsupported film products. If a supported film is to be made, then adjustments to the process may be introduced, including the addition of a step of fitting a woven or knitted liner onto the former prior to dipping into the elastomeric film-forming composition. In such cases, there is the option to use a coagulant dip step, or the coagulant dip step can be omitted.

The elastomeric film-forming composition used for dip formation of the article, such as a glove, may in some embodiments have a total solids content of between about 5 and 50%, such as between 5 and 40%. However, the total solids content can be higher. For example, where articles are produced using other process such as extrusion or moulding, a thermoplastic elastomer may be used, and the total solids content can be up to 100%.

One suitable method for producing a product in a dipping process may comprise:

Dipping a former into a coagulant comprising cationic multivalent ions, such as a calcium coagulant, to produce a coagulant-coated former;

Dipping the coagulant-coated former into an elastomeric film-forming composition described above, containing a viscosity modifier, with stirring and optionally sonication of the elastomeric film-forming composition to maintain the dispersion of the particles in the composition;

Optionally repeating the dipping step one or more times, with drying or partial drying before each subsequent dipping step;

Drying and/or curing the elastomeric film-forming composition to produce the elastomeric article.

As noted above, if a supported film product, such as a supported glove, is being made, then the coagulant dipping step in the above process outline may be performed, or it may be removed. In addition, there is the option to conduct this with or without heat sensitizer. The former may be fitted with a liner (e.g. woven or knitted liner), which may or may not have a layer of coagulant on its surface (and is optionally with or without a heat sensitizer), and then the former with the fitted liner is dipped into an elastomeric film-forming composition, followed the other steps described.

Further details on the basic process steps in some embodiments are as follows:

Optional Step (a) Dipping the Former into a Coagulant Containing Multivalent Ions in Solution A suitable former, which is based on the shape of the article to be produced (e.g. flat for a film or glove-shaped for a glove) is dipped into a coagulant containing multivalent ions in solution. The former is dipped into a coagulant containing multivalent ions, leaving a thin coating of the charged ions on the surface of the former. The charged ions coating can assist in controlling the amount of composition for forming the elastomeric film that will subsequently remain on the surface of the mould after dipping into the composition, through charge interactions. Cationic multivalent ion-containing coagulates are typically used, such as a calcium coagulant. The concentration of multivalent ions in the coagulant can broadly be in the range of 0.0-25% by weight of the coagulant solution (measured as the compound of the multivalent ion in the solution of the multivalent ions).

Optional Step (b) Drying or Partially Drying the Coagulant-Dipped Former

If the former is dipped into a coagulant, following this step the former is dried or partially dried.

Step (I) Dipping the Former into the Elastomeric Film-Forming Composition to Produce a Layer of Elastomeric Film-Forming Composition on the Mould The former is dipped into the composition for producing an elastomeric film, embodiments of which have been described in detail above. The duration of dipping, temperature, and former surface temperature may be as described in the PCT publications referred to above. If a supported film is being made, then there may be a prior step of fitting a liner on the former.

Step (ii) Drying or Partially Drying the Layer of Elastomeric Film-Forming Composition on the Former The conditions and details of this step may be as described in the PCT publications referred to above. The method of manufacture described herein encompasses the preparation of single layered or multiple-layered elastomeric films. Therefore, in some embodiments, the method may include step (v), which involves drying and curing the layered elastomeric film on the former directly after this step to prepare a single layered elastomeric film. In other embodiments, the method may include a number of repetitions of optional steps (iii) and (iv) after this step to produce a multiple-layered elastomeric film.

Step (iii) Optional Step of Dipping the Former Coated with the Dried or Partially Dried Layer of Elastomeric Film-Forming Composition into the Elastomeric Film-Forming Composition to Produce a Further Layer of Elastomeric Film-Forming Composition on the Former This step is optional, and is present when multi-layer articles are produced. The details of this step are as described in the PCT publications referred to above.

Step (iv) Optionally Repeating the Drying or Partial Drying Step (ii) and the Further Dipping Step (iii)

This step is optional, and is present when multi-layered articles are produced. The number of layers may be 2, 3 or more in multi-layered articles. The details of this step are as described in the PCT publications referred to above.

Step (v) Optional Additional Steps Prior to Drying and Curing

Further steps can be taken to fine-tune the manufacture of the elastomeric film or article. The details of these steps are as described in the PCT publications referred to above. In brief, the film or article can be leached to remove extractable components, there may be a coating material applied, beading/cuffing can be performed and/or the product may be passed through a curing or vulcanizing oven to evaporate the water in the film and enable better cross linking.

Step (vi) Drying and/or Curing the Layered Elastomeric Film on the Former

The details of this step are as described in the PCT publications referred to above.

Step (vii) Additional Steps

In any suitable sequence, addition optional steps that can be performed prior to stripping of the glove from the former include cooling, chlorination, post-curing rinsing, polymer coating and additional drying steps. The cured film may also be cooled/chlorinated/neutralized—post-leached in hot water and optionally dipped in lubricant solution or any silicone/silicone free polymers to enable easy stripping and better donning. Any optional coating layer that may be applied may additionally contain particles of type (a) and/or (b), although this is not particularly desired.

Step (viii) Stripping

The film or article is stripped from the former at the conclusion of the formation process. Optionally, the glove may be inverted after stripping to switch the inner layer to the exterior, according to need.

Metal Detector and X-Ray Detection

The articles of embodiments of the invention, or portions thereof of small volume (e.g. about at least 0.05 mm$^3$, such as about 0.08 mm$^3$, or at another portion size between 0.05-1.0 mm$^3$, or any sizes larger than 1.0 mm$^3$ are capable of detection by metal detectors and x-ray detectors, even with a background metal present, due to the presence of the particles of type (b). The detectable portion may be about 0.08, 0.1, 0.2, 0.3, 0.4, 0.5, 0.6, 0.7, 0.8, 0.9, 1.0, 2.0 or 5.0 mm$^3$ in size. The detectable volume may be converted into a particular area (based on the film thickness). For films having a thickness of 0.01-2 mm, a portion of the film with an area of between about 0.03 mm$^2$-100 mm$^2$ is preferably detectable. The detectable portion of a film of this thickness range may be of a size of about 0.05, 0.08, 0.1, 1, 10, 20, 30, 40, 50, 60, 70, 80, 90, 100, 200 or 500 mm$^2$ in area. A suitable metal detector to detect for the presence of the article or portion thereof is an Anritsu Duw-M5 Series KDB3005AHF Metal Detector System, which has a detection sensitivity of an iron ball having a diameter of 0.5 mm. A suitable x-ray detector is the Anritsu KD74 Series KD7416DWH X-ray inspection system.

Any article (or portion thereof) that produces a signal output indicative of the presence of metal in a metal detector, such as the metal detector system specified herein, is considered to be metal detectable. The signal output may be audio, visual or otherwise, as per the type of metal detector used. Any article (or portion thereof) that produces a signal output in an x-ray detector that is greater than a baseline signal based on a comparative article sample that is free of particles (a) and (b) is considered to be x-ray detectable. (In the Examples, a glove produced from Formulation B which is free of particles (a) and (b) was used as the comparative article sample for setting the baseline. This formulation may be used for setting a comparative article sample for the purpose of determining x-ray detectability if no other comparative article sample can be determined.) Preferably, the article (or portion thereof) is x-ray detectable against a baseline of an aluminium foil of 0.06 mm thickness. In some embodiments, the article (or portion thereof) has higher x-ray detectability—being detectable against a baseline of an aluminium foil having 0.09 mm thickness. In the case of a portion, the size of the portion is as described above. The fact that very small portions of the articles can be detected in such detectors is notable.

The inclusion of particles (a(i)) and (b) in the articles of embodiments of the invention has been found to improve the migration test results compared to a like comparison product of the same thickness that is free of particles (a) and (b). In some embodiments, the articles have a migration test result of less than 10 mg/dm$^2$, as measured against a 50% ethanol: water mixture, in accordance with EN standard EN 1186. In some embodiments, the migration test result is less than 9, less than 8, less than 7 or less than 6 mg/dm$^2$. The migration test result may even be less than 4.0 mg/dm$^2$ for thinner gloves. This test is a measure of the migration of soluble and insoluble components of an article (a glove) into a food product, or a test-based equivalent. For articles intended for contact with food, it is important to have low migration results, and the articles of embodiments of the invention have been found to satisfy this requirement.

In the claims and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention. In addition, unless the context indicates otherwise, a reference to "a" specified feature should be interpreted as a reference to one or more of the specified features. Thus, "a viscosity modifier" refers to the presence of one or more such viscosity modifiers.

EXAMPLES

The invention will now be described in further detail with reference to the following non-limiting examples which involve the preparation of elastomeric film gloves.
General Procedure for Production of Elastomeric Gloves
In the examples set out below, the following general procedure was utilised to produce elastomeric gloves, unless indicated to the contrary.

1. Preparation of Cross-Linking Composition
For those examples containing a cross-linking composition, this was prepared as follows. One part sodium aluminate as the chosen multivalent metal source, together with 1 part sodium hydroxide and 1 part potassium hydroxide as alkali and 1 part glycerine as stabiliser, were combined with 6 parts of water. Then, one part of this initial concentrate was combined with 10 parts of water, to yield a cross-linking composition containing 96 parts water and 1 part of each of the sodium aluminate, NaOH, KOH and glycerine. The combination was heated at an elevated temperature (typically around 95° C., but anywhere from 80° C. to boiling point) to dissolve the multivalent metal, through the formation of negatively charged multivalent metal complex ions. The concentration of metal ions in the cross-linking compositions obtained was 0.66% or 0.33% by weight of total solution, respectively. The pH of the solution was in the range of about 12-13.

2. Preparation of Latex Composition
The elastomeric film-forming composition is prepared from the selected nitrile latex and other components as described in the particular example indicated below. Some examples contained the cross-linking composition described in step 1, and some did not. The latex formulations for producing particular layers of the film contain particles (a(i)), (a(ii)) or (b), or a combination. The steps involved to formulate the latex included:
    Formulating the cross-linking composition as per step 1 above (if present in the latex formulation);
    Combining a dispersion of the elastomer with the cross-linking agents including any sulphur and accelerator (and the solubilised ionic cross-linking agent of step 1, if used), followed by
    Adding particles (a(i)) and/or (a(ii)) and/or (b), followed by
    Adding viscosity modifier, followed by
    Stirring to homogenize the viscosity modifier throughout the composition and to distribute particles (a(i)) and/or (a(ii)) and/or (b) throughout the composition, and
    Diluting to reduce the total solids content for the formulation.

3. Washing
The formers are subjected to pre-washing, to remove any remaining residues following removal of a glove previously made on the former. The formers are cleaned in mild acid/alkali and hot water. The formers are then dried by blowing air by blowers or air curtains or using ovens with the hot air having temperature above 105° C.

4. Coagulant Dipping
The cleaned dry former is immersed in a coagulant bath, which contains a 0-50% by weight solution of calcium nitrate. The coagulant also contains wetting agents (0.001-1.0%) and antifoaming agents (0.001-1.0%). In some embodiments, coagulant dipping is not required. In the examples practiced here, the coagulant contained 7-15% calcium nitrate.

5. Dipping Step
The former, coated with dried coagulant, is dipped into a tank containing the latex composition described in step 2 above. The composition is maintained at temperature of around 20-35° C., and is constantly circulated in the tank. Sonication may be used to avoid bubbles.

6. Drying
The composition coated formers are gelled in a gelling oven at a temperature of about 80-300° C. and the duration of 2-300 seconds.

7. Pre-leaching

This step is optional. Pre-leaching was completed after the final dip into the latex composition followed by gelling. Pre-leaching is conducted by rinsing in warm water for a short period of time. The gelled film coating on the former is pre-leached in series of tanks at a temperature anywhere between ambient and 95° C. In the examples it was typically about 55° C.

8. Second Dipping Step

This step is optional, and is performed if a further layer of elastomeric film is to be formed on the initial layer of elastomeric film-forming composition. This step may optionally involve an additional coagulant-dip into a coagulant composition, such as a 1-10% calcium nitrate containing coagulant composition, prior to conducting the second dip. The additional coagulant-dip may be beneficial when there is a significant amount of particles (a(i)) and/or (a(ii)) and/or (b) in the second layer of elastomeric film-forming composition. It is also utilized in order to produce a second layer which has a similar thickness, or larger thickness compared to the first layer.

9. Gelling/Pre Leaching/Beading

This preleaching step is optional, and is performed as per this sequence in the case of multiple dipping of latex composition after forming a further layer of elastomeric film. The product following the second dipping step is subjected to gelling and pre-leaching and beading. In the case of on-line polymer coating the sequence is gelling/preleaching/polymer coating/beading.

In the case of single dipping of elastomer, preleaching is completed as described above. The product following the dipping step is subjected to gelling and pre-leaching and beading. In the case of on-line polymer coating the sequence is gelling/preleaching/polymer coating/beading.

The beading, drying and pre-leaching steps can be carried out in any order. The processes of beading and pre-cure leaching could be exchanged depending on the quality of cuff beading.

10. Curing

Curing was conducted at about 80° C.-150° C. for about 15-30 minutes, depending upon the film thickness and intended end product physical properties.

11. Post-Leaching/Lubricant/Final Drying/Stripping/Tumbling

In the case of a glove product, the cured elastomeric article may be subjected to one or more process steps including post-leaching, chlorination (noting that this could alternatively take place before curing), neutralisation, additional curing/surface treatment and/or lubricant application (e.g. through dipping into a lubricant composition).

Test Procedure

For all the Examples, tests were performed to determine the following properties of the films:

Modulus at 100%, 300% and/or 500% elongation;
Tensile strength (M Pa/Psi) (1 MPa=145 Psi);
Elongation (%); and
Load at Break (N).

Tensile strength, stress at 100%, 300% and/or 500% modulus and elongation to break were measured by testing procedures conducted in accordance with ASTM D 412-06a (2013), based on the sample size set by the standard for gloves. The gloves were also tested for load at break (or force at break) measured in accordance with EN 455. The standards are readily available. These tests can be applied to multilayer films and gloves (such as examination gloves for medical applications). In all tables of results, the values indicated for the tensile strength and modulus are in units of MPa, load at break in N, and the elongation (or elongation at break) in %.

General Formulation

Set out below are typical formulations for three different compositions involving different polymer latex types.

TABLE 1

| Ingredients | Parts per Hundred Rubber (phr)-Dry basis (unless otherwise indicated) |
| --- | --- |
| Nitrile polymer latex | 100 |
| pH adjuster (hydroxide) | 0.1-2.0 |
| Cross-linking composition, comprising: | Added in an amount to provide the following: |
| trivalent metal source | 0.01-5.0 |
| hydroxide (sodium, potassium and/or ammonium) | 0.1-5.0 |
| mechanical stabilizer | 0-5.0 |
| Covalent cross-linking agent (e.g. sulphur) | 0.0-4.0 |
| Activator-Ionic cross-linking agent (e.g. ZnO) | 0.0-4.0 |
| Accelerator (ZDBC) | 0.0-5.5 |
| Antioxidant | 0.2-3.0 |
| Particles (a(i)) and/or (a(ii)) and/or (b) | 0.1-50 |
| Opaqueness provider | 0.0-5.0 (when present, 0.01-5.0) |
| Viscosity modifier | 0.1-6 |
| Pigment | As per requirement |
| Defoamer | 0-2.0, and if present 0.001-2.0 |

References to an amount of cross-linking composition in a phr amount above relates to the amount of each of the trivalent metal source, and the hydroxide, on a phr basis with respect to 100 parts of the nitrile polymer.

TABLE 2

| Ingredients | Parts per Hundred Rubber (phr)-Dry basis (unless otherwise indicated) |
| --- | --- |
| Natural rubber latex | 100 |
| pH adjuster (hydroxide) | 0.01-1.0 |
| Cross-linking composition, comprising: | Added in an amount to provide the following: |
| trivalent metal source | 0.01-5.0 |
| hydroxide (sodium, potassium and/or ammonium) | 0.1-5.0 |
| mechanical stabilizer | 0-5.0 |
| Covalent cross-linking agent (e.g. sulphur) | 0.0-4.0 |
| Activator-Ionic cross-linking agent (e.g. ZnO) | 0.0-4.0 |
| Accelerator (ZDBC, ZDEC) | 0.0-5.5 |
| Antioxidant | 0.2-3.0 |
| Particles (a(i)) and/or (a(ii)) and/or (b) | 0.1-50 |
| Opaqueness provider | 0.0-5.0 (when present, 0.01-5.0) |
| Inorganic filler | 0.1-50 |
| Viscosity modifier | 0.1-6 |
| Pigment | As per requirement |
| Wax | 0.0-5.0 |
| Defoamer | 0-2.0, and if present 0.001-2.0 |

TABLE 3

| Ingredients | Parts per Hundred Rubber (phr)-Dry basis (unless otherwise indicated) |
| --- | --- |
| Polychloroprene latex | 100 |
| pH adjuster (hydroxide) | 0.1-2.0 |

TABLE 3-continued

| Ingredients | Parts per Hundred Rubber (phr)-Dry basis (unless otherwise indicated) |
|---|---|
| Cross-linking composition, comprising: | Added in an amount to provide the following: |
| trivalent metal source | 0.01-5.0 |
| hydroxide (sodium, potassium and/or ammonium) | 0.1-5.0 |
| mechanical stabilizer | 0-5.0 |
| Covalent cross-linking agent (e.g. sulphur) | 0.0-1.5 |
| Activator-Ionic cross-linking agent (e.g. ZnO) | 0.0-6.0 |
| Accelerator (ZDBC, ZDEC, DPG) | 0.0-5.5 |
| Antioxidant | 0.2-3.0 |
| Particles (a(i)) and/or (a(ii)) and/or (b) | 0.1-50 |
| Opaqueness provider | 0.0-5.0 (when present, 0.01-5.0) |
| Inorganic filler | 0.1-50 |
| Viscosity modifier | 0.1-6 |
| Pigment | As per requirement |
| Wax | 0.0-5.0 |
| Defoamer | 0-2.0, and if present 0.001-2.0 |

Example 1

Particle blends were prepared as follows:

TABLE 4

| | Multi-detectable particles | | |
|---|---|---|---|
| Material | Particles of type (a(i)) e.g. magnetite or coated iron (%) | Particles of type (a(ii)) e.g. coated aluminium (%) | Particles of type (b) e.g. bismuth oxide or tungsten (%) |
| MDP 1 | 10 | 0 | 90 |
| MDP 2 | 30 | 0 | 70 |
| MDP 3 | 50 | 0 | 50 |
| MDP 4 | 70 | 0 | 30 |
| MDP 5 | 90 | 0 | 10 |
| DP 6 | 100 | 0 | 0 |
| DP 7 | 30 | 70 | 0 |

In the Examples demonstrated here, the particles of type (a(i)) were magnetite particles having a mass mean particle size of 0.8 μm (D50) for MDP1-MDP5, or coated iron particles having a mass mean particle size of 1.5 μm (D50) for DP6 and DP7. The particles of type (a(ii)) were coated aluminium particles having a mass mean particle size of 11 μm (D50) and the particles of type (b) were tungsten or bismuth oxide particles having a mass mean particle size of 1.5 μm (D50). Tungsten particles were used in Examples 1, 2 and 8, while bismuth oxide was used in Examples 3, 4, 5, 6 and 7.

Seven formulations were prepared for use in different combinations to produce articles with different arrangements of layer(s) and particle compositions, as follows:

Formulation A: For the production of a metallic grey layer with multi-detectable particle blend of (a(i)) and (b) based on MDP 1:

TABLE 5

| Formulation A: Nitrile compound with MDP 1 | |
|---|---|
| Material | Amount (phr) |
| Nitrile latex | 100 |
| Potassium hydroxide | 1.7 |

TABLE 5-continued

| Formulation A: Nitrile compound with MDP 1 | |
|---|---|
| Material | Amount (phr) |
| Ionic crosslinking agent (Sodium aluminate; composition also containing sodium hydroxide, glycerine) | 0.1 |
| Covalent crosslinker (Sulphur) | 0.2 |
| Accelerator (ZDBC) | 0.2 |
| Antioxidant | 0.3 |
| MDP 1 – magnetite + tungsten | 40 |
| Opacifier | 3.0 |
| Viscosity modifier (pseudoplastic acrylic based emulsion) | 6.0 |
| pH adjuster | 0.6 |

Viscosity at 25° C., spindle 3, 30 rpm: 332 cps

The formulation was also produced with the same components as listed above, but with lower amounts of viscosity modifier and pH adjuster (4.0 and 0.4 phr, respectively).

Formulation B: For the production of a blue-toned layer without particles (a(i)), (a(ii)) and (b)

TABLE 6

| Formulation B: Nitrile compound without particles (a) and (b) | |
|---|---|
| Material | Amount (phr) |
| Nitrile latex | 100 |
| Potassium hydroxide | 1.7 |
| Ionic crosslinking agent (sodium aluminate) | 0.1 |
| Covalent crosslinker (Sulphur) | 0.2 |
| Accelerator (ZDBC) | 0.2 |
| Antioxidant | 0.4 |
| Opacifier | 3.0 |
| Pigment (Blue) | 0.2 |

Formulation C: For the production of a metallic grey layer containing multi-detectable particle blend of (a(i)) and (b) based on MDP 2:

TABLE 7

| Formulation C: Nitrile compound with MDP 2 | |
|---|---|
| Material | Amount (phr) |
| Nitrile latex | 100 |
| Potassium hydroxide | 1.7 |
| Ionic crosslinking agent (sodium aluminate) | 0.1 |
| Covalent crosslinker (Sulphur) | 0.2 |
| Accelerator (ZDBC) | 0.2 |
| Antioxidant | 0.3 |
| MDP 2 – magnetite + tungsten | 56.7 |
| Viscosity modifier (pseudoplastic acrylic based emulsion) | 7.0 |
| pH adjuster | 0.7 |

Viscosity at 25° C., spindle 3, 30 rpm: 372 cps

The above formulation was also produced with the same components as listed above, but with lower amounts of viscosity modifier and pH adjuster (4.0 and 0.4 phr, respectively).

Formulation D: For the production of a metallic grey layer containing multi-detectable particle blend of (a(i)) and (b) based on MDP 3:

TABLE 8

| Formulation D: Nitrile compound with MDP 3 | |
| --- | --- |
| Material | Amount (phr) |
| Nitrile latex | 100 |
| Potassium hydroxide | 1.7 |
| Ionic crosslinking agent (sodium aluminate) | 0.1 |
| Covalent crosslinker (Sulphur) | 0.2 |
| Accelerator (ZDBC) | 0.2 |
| Antioxidant | 0.3 |
| MDP 3 – magnetite + tungsten | 42 |
| Viscosity modifier (pseudoplastic acrylic based emulsion) | 6.5 |
| pH adjuster | 0.7 |

Viscosity at 25° C., spindle 3, 30 rpm: 416 cps

The formulation was also produced with the same components as listed above, but with lower amounts of viscosity modifier and pH adjuster (4.5 and 0.5 phr, respectively).

Formulation E: For the production of a metallic grey layer containing multi-detectable particle blend of (a(i)) and (b) based on MDP 5:

TABLE 9

| Formulation E: Nitrile compound with MDP 5 | |
| --- | --- |
| Material | Amount (phr) |
| Nitrile latex | 100 |
| Potassium hydroxide | 1.7 |
| Ionic crosslinking agent (sodium aluminate) | 0.1 |
| Covalent crosslinker (Sulphur) | 0.2 |
| Accelerator (ZDBC) | 0.2 |
| Antioxidant | 0.3 |
| MDP 5 - magnetite + tungsten | 45 |
| Viscosity modifier (pseudoplastic acrylic based emulsion) | 7.0 |
| pH adjuster | 0.7 |

Viscosity at 25° C., spindle 3, 30 rpm: 416 cps

The formulation was also produced with the same components as listed above, but with lower amounts of viscosity modifier and pH adjuster (4.5 and 0.5 phr, respectively).

Formulation F: For the production of a blue layer containing coated metal-detectable particles (a(i)) based on DP 6:

TABLE 10

| Formulation F: Natural rubber compound with DP 6 | |
| --- | --- |
| Material | Amount (phr) |
| Natural rubber latex | 100 |
| Potassium hydroxide | 1.0 |
| Activator (Zinc oxide) | 0.6 |
| Covalent crosslinking agent (Sulphur) | 1.0 |
| Accelerator (ZDBC/ZDEC) | 0.45 |
| Antioxidant | 0.6 |
| Coated iron particles | 10 |
| Opacifier | 1.5 |
| Pigment (blue) | 0.7 |
| Viscosity modifier (xanthan gum) | 2.0 |

Viscosity at 25° C., spindle 3, 30 rpm: 416 cps

Formulation G: For the production of a blue polychloroprene rubber layer containing coated metal detectable particles (a(i)) and (a(ii)) based on DP 7:

TABLE 11

| Formulation G: Polychloroprene compound with MDP 7 | |
| --- | --- |
| Material | Amount (phr) |
| Polychloroprene latex | 100 |
| Potassium hydroxide | 1.7 |
| Surfactant (sulfated alkyloleate/SLES) | 1.0 |
| Ionic crosslinking agent (ZnO) | 7 |
| Covalent crosslinking agent (Sulphur) | 1.5 |
| Accelerator (ZDBC) | 2.0 |
| Antioxidant | 2.0 |
| Coated iron particles | 10 |
| Coated aluminium particles | 20 |
| Opacifier | 2.0 |
| Pigment (Blue) | 0.3 |
| Viscosity modifier (pseudoplastic acrylic based emulsion) | 4.5 |
| pH adjuster | 0.5 |

Viscosity at 25° C., spindle 3, 30 rpm: 476 cps

The following combinations of layers can be prepared using the above seven formulations, or variants thereof. Sample gloves were produced based on some of the combinations listed below, and were subjected to testing. The results of those tests are presented further below.

TABLE 12

| Single-layered | Double-layered | More than 2 layers |
| --- | --- | --- |
| (i) Multi-detectable particles throughout layer. Produced using Formulation A, C, D, E, F or G. | (i) Multi-detectable particles or metal detectable particles throughout both layers. Each layer can be of Formulation A, C, D, E, F or G. | (i) Multi-detectable or metal detectable particles throughout all layers. Each layer can be of Formulation A, C, D, E, F or G. |

TABLE 12-continued

| Single-layered | Double-layered | More than 2 layers |
|---|---|---|
| (ii) Metal-detectable particles throughout layer. Produced using Formulation A, C, D, E, F or G. | (ii) Multi-detectable particles or metal detectable particles in one of the layers (e.g. Formulation A, C, D, E, F or G) with another layer not containing detectable particles (e.g. Formulation B). | (ii) One or more layers containing multi-detectable particles or metal detectable particles (e.g. Formulation A, C, D, E, F or G) in combination with one or more layers not containing detectable particles (e.g. Formulation B). Layers may be arranged in groups, randomly, or in an alternating manner. |
| — | (iii) Magnetic particles (a(i)) and/or conductive particles (a(ii)) in one layer according to possible dosages, and particles with high atomic mass (b) in another layer according to possible dosages. | (iii) One or more layers containing multi-detectable particles (e.g. Formulation A, C, D or E) in combination with layers containing only particles (a(i)) and/or particles (a(ii)), or only particles (b). Layers may be arranged in groups, randomly, or in an alternating manner. Additionally a layer not containing detectable particles (Formulation B) can be combined with the above. |
| — | — | (iv) One or more layers containing multi-detectable particles (Formulation A, C, D or E) in combination with one or more layers containing only particles (a(i)) and/or particles (a(ii)) (e.g. Formulations F or G) and one or more layers containing only particles (b). Layers may be arranged in groups, randomly, or in an alternating manner. Additionally, a layer not containing detectable particles (Formulation B) can be combined with the above. |
| — | — | (v) One or more layers containing only particles (a(i)) and/or particles (a(ii)) in combination with one or more layers containing particles (b). Layers may be arranged in groups, randomly, or in an alternating manner. Additionally, a layer not containing detectable particles (Formulation B) can be combined with the above. |

The arrangement of layers may dictate the appearance or final colour of the glove. As magnetic particles are known to impart a solid colour to the elastomeric layer, pigments can be added to layers where magnetic particles are present in small volumes or are entirely absent in the layer. Therefore, the elastomeric article may be produced in any colour other than metallic grey, according to intended appearance.

Gloves were produced from Formulations A, B, C, D, E, F and/or G as follows:

TABLE 13

| Glove Type | Formulation | Layers | Colour | Thickness (mm) |
|---|---|---|---|---|
| I | A | Double-layered (double-dipped) | Metallic grey | 0.10 |
| II | B | More than 2 layers (triple-dipped) | Blue | 0.15 |
| III | B and C | More than 2 layers (1st dipping: B; 2nd & 3rd dips: C) | Blue outer layer with metallic grey inner layer | 0.10 |
| IV | D | Double-layered (double-dipped) | Metallic grey | 0.10 |
| V | E | Double-layered (double-dipped) | Metallic grey | 0.10 |

TABLE 13-continued

| Glove Type | Formulation | Layers | Colour | Thickness (mm) |
|---|---|---|---|---|
| VI | F | Double-layered (double-dipped) | Blue | 0.08 |
| VII | G | Double-layered (double-dipped) | Blue | 0.08 |

The properties of the multi-detectable gloves so produced were tested and the results are set out below:

TABLE 14

| Physical properties of glove | Glove Type I | Glove Type II | Glove Type III | Glove Type IV | Glove Type V |
|---|---|---|---|---|---|
| Particle (a) content (wt %) | 2.6 | 0 | 8.3 | 13.3 | 24.1 |
| Particle (b) content (wt %) | 23.5 | 0 | 19.6 | 13.3 | 2.7 |
| Metal detection | Yes (min. 5.0 mm³) | No | Yes (min. 1.8 mm³) | Yes (min. 1.0 mm³) | Yes (min. 0.5 mm³) |

TABLE 14-continued

| Physical properties of glove | | Glove Type I | Glove Type II | Glove Type III | Glove Type IV | Glove Type V |
|---|---|---|---|---|---|---|
| X-ray detection | Baseline: Formulation B | Yes | No | Yes | Yes | Yes |
| | Baseline: 0.06 mm Al foil | Yes | No | Yes | Yes | Yes |
| | Baseline: 0.09 mm Al foil | Yes | No | Yes | Yes | No |
| | Baseline: 0.12 mm Al foil | Yes | No | Yes | Yes | No |

Figure 2:
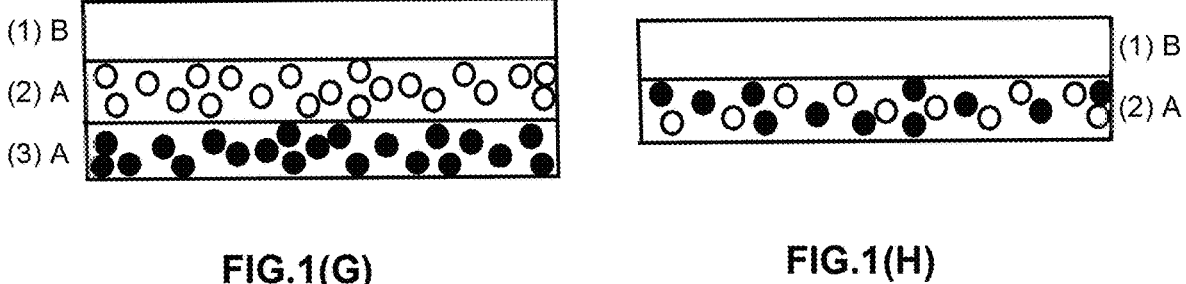
FIG. 2 is an X-ray image of square film samples taken from gloves produced in accordance with embodiments of the invention, and a comparative example. The samples indicated from left to right are those of type I, III, IV, V and II (II being the comparative example).
Figure 2:
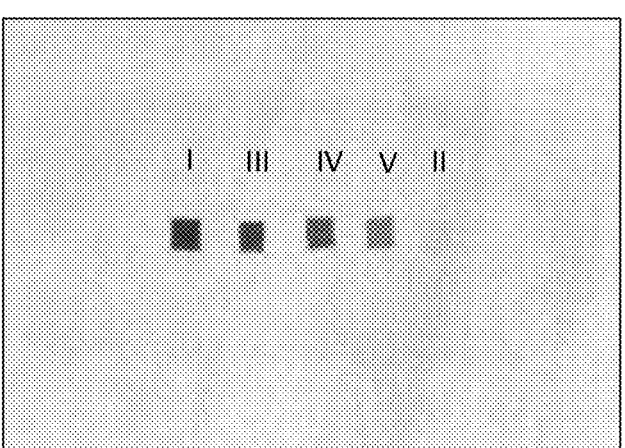
Figure 3:
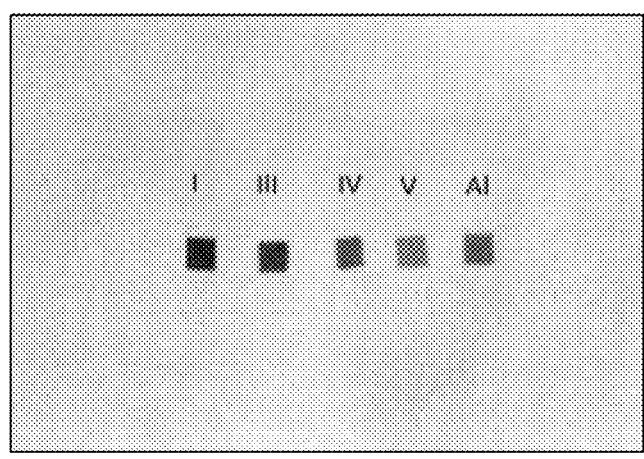
FIG. 3 is an X-ray image taken of four of the same square film samples as tested in FIG. 2 (from left to right I, III, IV and V), followed by a 0.12 mm thick aluminium foil square (far right).
Figure 4:
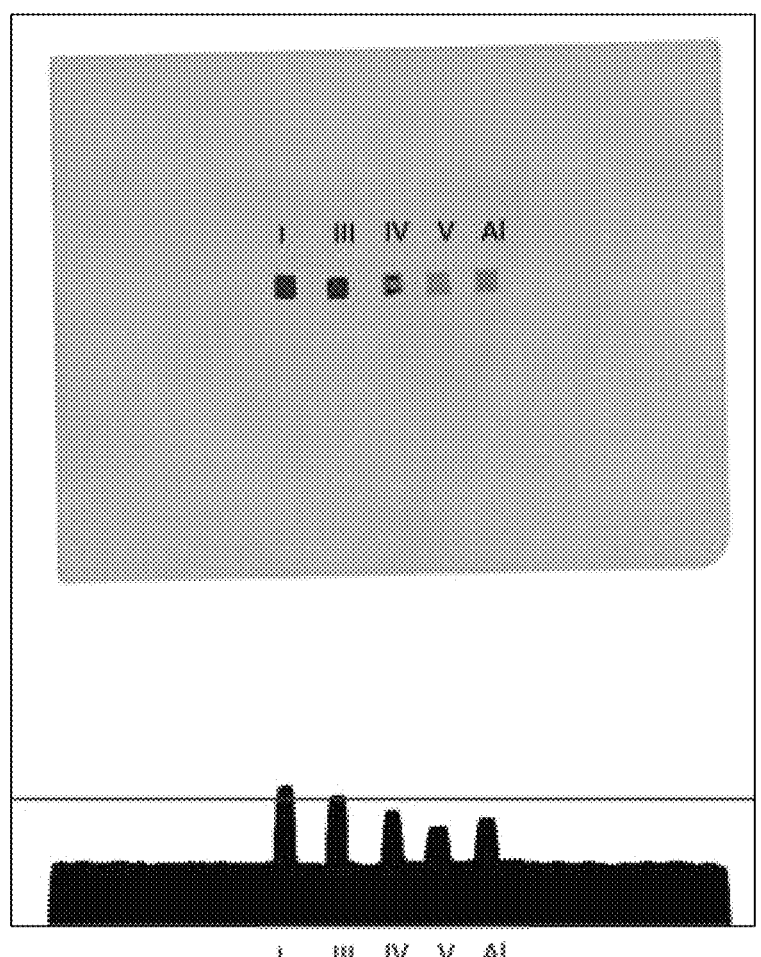
FIG. 4 shows the same X-ray image as that of FIG. 3, with a correlating bar graph below the X-ray image to show the detection intensity (Y-axis peaks) for each sample (I, III, IV and V), compared to the 0.12 mm thick aluminium film (marked Al).

The X-ray image taken of 100 mm$^2$ samples of films I to V is provided as FIG. 2. The X-ray images were all generated by an Anritsu KXS7534AVCLE X-ray inspection system. On the X-ray image, those areas that have attenuated the x-ray beam appear darker. The order of films illustrated in this figure is, from left to right, I, III, IV, V and II. Glove type II, despite being 50% thicker, is virtually non-detectable by this x-ray imaging. FIG. 3 is an X-ray image taken of the same squares of films (from left to right I, III, IV and V), with an aluminium foil square of the same size positioned as the last of the squares imaged. This shows that gloves of types I and III which have the highest amounts of particle (b) are darkest (most readily detectable), and the darkness reduces as the amount of particles (b) decreases. FIG. 4 shows the same x-ray image as that of FIG. 3, with a correlating graph below the X-ray image to show the detection intensity (Y-axis peaks), compared to the 0.12 mm thick aluminium film. Film V had lower intensity, and films I, III and IV had higher intensity than the aluminium film (such that where aluminium film of 0.12 mm thickness is the baseline, these films I, III and IV are detectable). Films I and III had a detection intensity such that they were above a threshold level marked by the horizontal line on the graph. The properties of the metal-detectable gloves (containing magnetic particles alone or in combination with high conductivity particles) were tested and the results are set out below:

TABLE 15

| Physical properties of glove | Glove Type VI | Glove Type VII |
|---|---|---|
| Particle (a(i)) content (wt %) | 7.1 | 6.1 |
| Particle (a(ii)) content (wt %) | 0 | 14.4 |
| Metal detection | Yes (min. 2.0 mm$^3$) | Yes (min. 2.0 mm$^3$) |

The amount of particles (a(i)) can be about 1 wt % or above of the glove, or 2.0 wt % and above, given that even gloves of 0.1 mm thickness with 2.6 wt % of those particles were metal detectable. Amounts of at least 5, 8, 10, 13 and 20 wt % improve detectability by metal detectors. It is desirable for the amount of particles (a(ii)) to be above 10.0 wt % to provide metal detectability, preferably at least 14, 17 or 20 wt %. It is desirable for the amount of particles (b) to be above about 2.7 wt %, based on the test data, to provide x-ray detectability. The amount is preferably at least 7 wt %, 10 wt % or at least 12 wt %, or at least 13.5 wt %. The amounts may vary for products of different film thicknesses, but these figures provide a workable range.

Example 2

It is noted that the film of type IV tested in Example 1 is detectable by X-ray above the baseline of three different thicknesses of aluminium foil. A test was conducted as follows to investigate the extent to which the viscosity modifier has any impact on the detectability of the film.

In this Example, a modified version of film IV was prepared (referred to as IV(a)), having the same formulation as film IV, but with the viscosity modifier removed. The thickness of the films produced was the same. The properties of film IV(a) were tested and tabulated against the properties of Film IV in the table below:

TABLE 16

| Physical properties of detectable glove | | Glove Type IV | Glove Type IV(a) without viscosity modifier |
|---|---|---|---|
| Thickness (mm) | | 0.10 | 0.10 |
| Particle (a(i)) content (phr) | | 20 | 20 |
| Particle (b) content (phr) | | 20 | 20 |
| Metal detection | | Yes (min. 1.0 mm$^3$) | No |
| X-ray detection | Baseline: Formulation B | Yes | No |
| | Baseline: 0.06 mm Al foil | Yes | No |
| | Baseline: 0.09 mm Al foil | Yes | No |
| | Baseline: 0.12 mm Al foil | Yes | No |

It was remarkable, and notable, that the presence of the viscosity modifier had a significant impact on the detectability of the glove by both metal detection and x-ray detection.

Example 3

In Example 3, tests were performed on two different latex formulations (different elastomers and cross-linking agent combinations), and with two different viscosity modifiers, to explore the impact of changing the class of viscosity modifier, the type of elastomer and the choice of cross-linking agent combination.

The viscosity modifiers tested were of the following classes:

a. An alkali swellable emulsion (ASE) type thickener which is a dispersion of acid-functional acrylic polymers in water (i.e. the pseudoplastic acrylic based emulsion thickener used in Example 1) e.g. Rheovis AS1125.

b. A polysaccharide which has a main chain structure identical to that of cellulose e.g. xanthan gum.

The elastomers and cross-linking agent combinations tested were of the following classes:

i. Nitrile latex, with sodium aluminate, sulphur and ZDBC.

ii. Natural rubber latex, with ZnO, sulphur and ZDBC.

Formulations containing a varying amount and identity of viscosity modifier (those amounts and identities being indicated in the tables following the formulation table) were produced and tested. The viscosity of each formulation was tested at 25° C. using the Brookfield Viscometer, with Spindle No. 3 at 30 rpm. The viscosity was also tested under the same conductions but at 60 rpm spindle speed, or using a different spindle, where the viscosity was such that a different spindle was warranted.

TABLE 17

Nitrile latex formulation for viscosity modifier test:

| Material | Amount (phr) |
|---|---|
| Nitrile latex | 100 |
| Potassium hydroxide | 1.7 |
| Ionic crosslinking agent (sodium aluminate) | 0.1 |
| Covalent crosslinker (Sulphur) | 0.2 |
| Accelerator (ZDBC) | 0.2 |
| Antioxidant | 0.3 |
| MDP 5 - magnetite + bismuth oxide | 10 |
| Viscosity modifier - as per tables 19(a) and (b) below | As per tables 19(a) and (b) below |
| pH adjuster | As needed for a pH between 9-10 |

TABLE 18

Natural rubber latex formulation for viscosity modifier test:

| Material | Amount (phr) |
|---|---|
| Natural rubber latex | 100 |
| Potassium hydroxide | 1.0 |
| Covalent crosslinker (Sulphur) | 0.4 |
| Accelerator (ZDBC) | 0.2 |
| Activator (ZnO) | 0.2 |
| Antioxidant | 0.3 |
| MDP 5 - magnetite + bismuth oxide | 10 |
| Viscosity modifier - as per table 20 below | As per table 20 below |
| pH adjuster | As needed for a pH between 9 and 10. |

TABLE 19a

| (a) ASE thickener - dosage (phr) | Spindle No. | Viscosity, measured after 24 hours (cps) 30 rpm | 60 rpm | Sedimentation/appearance |
|---|---|---|---|---|
| 0 | 1 | 9.8 | 8.3 | Immediate and complete sedimentation |
| 3.0 | 2 | 44.0 | 37.5 | Complete sedimentation after a few minutes |
| 3.3 | 2 | 79.0 | 63.5 | Slight settling after 24 hours |
| 3.5 | 3 | 263.9 | 110.0 | Slight settling after 7 days |
| 4.0 | 3 | 295.9 | 214.0 | Not evenly distributed, no sedimentation after 7 days |
| 4.5 | 3 | 535.9 | 357.9 | Evenly distributed, no sedimentation after 7 days |
| 5.0 | 3 | 1084.0 | 693.9 | Evenly distributed, no sedimentation after 7 days |
| 7.0 | 3 | 1888.0 | 1168.0 | Very thick texture, high presences of air bubbles |

TABLE 19(b)

| (b) Poly-saccharide thickener - dosage (phr) | Spindle No. | Viscosity after 24 hours (cps) 30 rpm | 60 rpm | Sedimentation/appearance |
|---|---|---|---|---|
| 0 | 1 | 9.8 | 8.3 | Immediate and complete sedimentation |
| 1.0 | 3 | 100.0 | 54.0 | Complete sedimentation after a few hours |

TABLE 19(b)-continued

| (b) Poly-saccharide thickener - dosage (phr) | Spindle No. | Viscosity after 24 hours (cps) 30 rpm | 60 rpm | Sedimentation/appearance |
|---|---|---|---|---|
| 1.5 | 3 | 140.0 | 100.0 | Slight settling after a few hours |
| 2.0 | 3 | 332.0 | 222.0 | Slight settling after 3 days |
| 2.5 | 3 | 468.0 | 290.0 | Slight settling after 4 days |
| 3.5 | 3 | 884.0 | 508.0 | Evenly distributed, no sedimentation after 7 days |
| 4.0 | 3 | 1116.0 | 634.0 | Thick texture, evenly distributed, no sedimentation after 7 days |
| 5.0 | 3 | 2092.0 | 1154.0 | Very thick texture, high presences of air bubbles |

TABLE 20

Natural rubber latex compound

| Poly-saccharide thickener - dosage (phr) | Spindle No. | Viscosity after 24 hours (cps) 30 rpm | 60 rpm | Sedimentation/appearance |
|---|---|---|---|---|
| 0 | 1 | 10.5 | 9.3 | Immediate and complete sedimentation |
| 0.5 | 2 | 28.0 | 22.5 | Sedimentation after 24 hours |
| 1.0 | 3 | 100 | 70 | Unevenly distributed, begin to settle after 7 days |
| 1.5 | 3 | 220 | 142 | No sedimentation after 5 days |
| 2.5 | 3 | 472 | 288 | Evenly distributed, no sedimentation after 7 days |
| 4.0 | 3 | 948 | 556 | Thick texture, evenly distributed, no sedimentation after 7 days |

Nitrile gloves of good quality, and with a good even distribution of the MDP particles, were able to be produced using 3.3, 3.5 phr, 4.0 phr, 4.5 phr and 5.0 phr of ASE-type thickener, or with 1.0, 1.5, 2.0, 2.5, 3.5 or 4.0 phr of polysaccharide-type thickener, provided dipping took place within a suitable time-period (i.e. prior to the sedimentation indicated in the comments). Natural rubber latex gloves of good quality, with a good even distribution of the MDP particles were also able to be produced using around 1.0, 1.5, 2.5 or 4.0 phr of polysaccharide thickener.

All thickeners imparted pseudoplastic properties to the dipping formulation. By way of example, 5.0 phr of the ASE thickener gave a viscosity of 1084 cps at 30 rpm, and this reduced by 36% to 639.9 cps after stirring at 60 rpm. The polysaccharide thickener generally had a greater impact on increasing the viscosity at lower dosages compared to ASE-type thickener, due to which control of viscosity by dosage is difficult compared to the ASE-type thickener. Based on the viscosity obtained at 30 rpm (Spindle No. 1, 2 and 3) the range of suitable viscosity is between 50 to 1200 centipoise. It is most desirable to select a viscosity modifier, and to select the amount to be used, based on the achievement of a viscosity at 30 rpm (Spindle No. 3) between about 250 and 1000, preferably between 250 and 500 centipoise for nitrile latex. A viscosity within the range of about 250 to 1000 is preferred as the composition was successfully stabilized to ensure complete distribution of the particles throughout the composition. On this basis, for nitrile gloves, the ASE-type and polysaccharide-type thickeners at around 4.5 and 3.5 phr, respectively, produced the best results for a composition having 15% TSC. For natural rubber latex the amount of polysaccharide thickener is preferably about 2.0-4.0 phr. It is noted that changing the total solids content would impact on the amount of thickener that is most suited to achieve the desired viscosity level. The total solids content of the formulations of Tables 17 and 18 was 15%.

Example 4

Formulation H containing multi-detectable particles was prepared, and used to produce double-layer and single-layer gloves, denoted gloves VIII and IX, respectively. The magnetite particles had a mean particle size as indicated for the preceding examples, and the bismuth oxide particles had a mean particle diameter (D50) of 1.6 μm. The physical properties of the gloves were tested and the test results are presented below.

Formulation H: For the production of a metallic grey layer containing multi-detectable particle blend of (a(i)) and (b) based on MDP 4:

TABLE 21

| Formulation H: Nitrile compound with MDP 4 | |
| --- | --- |
| Material | Amount (phr) |
| Nitrile latex | 100 |
| Potassium hydroxide | 1.7 |
| Ionic crosslinking agent (sodium aluminate) | 0.15 |
| Covalent crosslinking agent (Sulphur) | 0.2 |
| Accelerator (ZDBC) | 0.2 |
| Antioxidant | 0.3 |
| MDP 4 - Magnetite + bismuth oxide | 30 |
| Opacifier | 3.0 |
| Viscosity modifier (pseudoplastic acrylic based emulsion) | 6.0 |
| pH adjuster | 0.6 |

Viscosity at 25° C., spindle 3, 30 rpm: 476 cps

The formulation was also produced with the same components as listed above, but with lower amounts of viscosity modifier and pH adjuster (4.5 and 0.5 phr, respectively).

The gloves were produced from Formulation H in accordance with the following parameters:

TABLE 22

| Glove Type | Formulation | Layers | Colour | Thickness (mm) |
| --- | --- | --- | --- | --- |
| VIII | H | Double-layered | Metallic grey | 0.08 |
| IX | H | Single-layered | Metallic grey | 0.03 |

The physical properties of the gloves were as follows:

TABLE 23

| Physical properties of glove | Glove Type VIII | Glove Type IX | Glove Type IX repeat |
| --- | --- | --- | --- |
| Particle (a(i)) content (%) | 14.1 | 14.1 | 14.1 |
| Particle (b) content (%) | 6.0 | 6.0 | 6.0 |
| Tensile strength (MPa) | 27.0 | 18.1 | 21 |
| Modulus at 100% (MPa) | 3.9 | 4.4 | 4.3 |
| Modulus at 300% (MPa) | 7.2 | 7.3 | 7.2 |

TABLE 23-continued

| Physical properties of glove | | Glove Type VIII | Glove Type IX | Glove Type IX repeat |
| --- | --- | --- | --- | --- |
| Modulus at 500% (MPa) | | 15.4 | 14.9 | 14.5 |
| Elongation at break (%) | | 608 | 530 | 560 |
| Metal detection | | Yes (min. 1.0 mm³) | Yes (min. 1.0 mm³) | Yes (min. 1.0 mm³) |
| X-ray detection | Baseline: Formulation B | Yes | Yes | Yes |
| | Baseline: 0.06 mm Al foil | Yes | No | No |
| | Baseline: 0.09 mm Al foil | No | No | No |
| | Baseline: 0.12 mm Al foil | No | No | No |

Note that detectability is measured against different "baselines"—including (a) the baseline of a formulation without any detectable particles (i.e. gloves made from Formulation B as the baseline), and (b) the baselines of three different thicknesses of aluminium foil. Gloves of Type VIII and IX have a high filler loading of 30 phr, and both gloves are able to provide good physical properties despite the high loading and low thickness.

The examples demonstrate that articles, and gloves in particular, are able to be produced with sufficiently high detectability (even based on low test sample/portion sizes), while remaining very thin to provide sufficiently high tactile sensitivity when worn by the user. The examples demonstrate the effective production of very thin gloves—around 0.04 mm thickness—which are still detectable even at low portion area sizes. Thinness and tactile sensitivity are important features to ensure that the gloves will achieve consumer/workplace acceptance. Achieving a balance between high-detectability of the gloves, with low thickness and good tactile properties (strength, modulus), was a significant achievement.

Example 5

Double-layer gloves were produced from Formulation I, and compared to gloves of type VIII described above produced from Formulation H. Formulation I was prepared as follows:

TABLE 24

| Formulation I: Nitrile latex with MDP 4 | | |
| --- | --- | --- |
| Material | Amount (phr)-Variant (i) | Variant (ii) |
| Nitrile latex | 100 | 100 |
| Potassium hydroxide | 1.7 | 1.7 |
| Covalent crosslinking agent (Sulphur) | 0.5 | 1.5 |
| Activator (ZnO) | 1.1 | 0.8 |
| Accelerator (ZDBC) | 1.0 | 0.8 |
| Antioxidant | 0.25 | 0.25 |
| MDP 4 – Magnetite + bismuth oxide | 30 | 30 |
| Opacifier | 2.5 | 2.5 |
| Viscosity modifier (pseudoplastic acrylic based emulsion) | 6.0 | 4.5 |
| pH adjuster | 0.6 | 0.5 |

The viscosity modifier was present in Formulation I in an amount to provide the latex composition, at a total solids content of 15%, with a viscosity of 480 cps, spindle 3, at 30 rpm. The original version of the formulation used for earlier test work is marked as variant (i). A modified version was also prepared with lower amounts of the cross-linking agents ZnO and ZDBC, which is described as variant (ii). Variant 2 had a slightly lower viscosity than variant (i), due to the lower amount of viscosity modifier.

Gloves denoted type X were produced from Formulation I (using the two variants on the formulations, and thus also marked X(i) and X(ii)). The properties were tested, and those properties were compared to the properties of glove type VIII produced from Formulation H. The properties are summarised in the following table:

TABLE 25

| Physical properties of glove | Glove Type VIII (Formulation H) | Glove Type X(i) (Formulation I) | Glove Type X(ii) (Formulation I) with lower x-linker amount) |
|---|---|---|---|
| Thickness (mm) | 0.08 | 0.08 | 0.08 |
| Particle (a(i)) content (phr) | 20 | 20 | 20 |
| Particle (b) content (phr) | 10 | 10 | 10 |
| Metal detection | Yes (min. 1.0 mm³) | Yes (min. 1.0 mm³) | Yes (min. 1.0 mm³) |
| X-ray detection | Yes | Yes | Yes |
| Tensile strength (MPa) | 27 | 25 | 24 |
| Modulus at 100% (MPa) | 3.9 | 2.1 | 1.9 |
| Modulus at 300% (MPa) | 7.2 | 5.1 | 5.5 |
| Elongation at break (%) | 608 | 530 | 558 |

Table 25 shows different formulations that support similar phr loadings of detectable particles (a) and (b). Both films were of the same thickness. The cross-linking agent combination (and or amounts used) was different as between the formulations, but the results show that the overall glove properties were good, regardless of this difference. Glove type X (both of variants (i) and (ii)) had lower elongation at break than glove type VIII, but still within acceptable range, and the tensile strength was similar between the products. Both were metal detectable and x-ray detectable at a minimum volume of 1.0 mm³.

Example 6

The gloves produced according to the formulations of the examples having detectable particles (a) and (b) are expected to come into contact with various surfaces in standard use, and may come into contact with food products in particular. For this reason, a study was conducted on the tendency for there to be migration of any soluble or insoluble materials in the glove. The overall migration limits of the gloves are illustrated in this example. Formulation J containing multi-detectable particles was prepared, and used to produce single-layer and double-layer gloves in accordance with the procedure described above, denoted gloves XI and XII, respectively.

Formulation J: For the production of a metallic grey layer containing multi-detectable particle blend of (a(i)) and (b) based on MDP 3:

TABLE 26

| Formulation J: Nitrile compound with MDP 3 | |
|---|---|
| Material | Amount (phr) |
| Nitrile latex | 100 |
| Potassium hydroxide | 1.7 |
| Ionic crosslinking agent (sodium aluminate) | 0.1 |
| Covalent crosslinking agent (Sulphur) | 0.2 |
| Accelerator (ZDBC) | 0.2 |
| Antioxidant | 0.3 |
| MDP 3 – Magnetite + bismuth oxide | 43 |
| Viscosity modifier (pseudoplastic acrylic based emulsion) | 6.5 (Glove Type XI) |
| | 4.5 (Glove Type XII) |
| | 0.7 (Glove Type XI) |
| pH adjuster | 0.5 (Glove Type XII) |

The gloves were produced from Formulation J, and a control glove was prepared from Formulation B in accordance with the following parameters:

TABLE 27

| Properties of composition for each glove type | | | |
|---|---|---|---|
| Glove Type | Formulation | Total Solid Content (%) | Viscosity at 25° C., spindle 3, 30 rpm (cps) |
| Control | B | 15 | No value detected |
| XI | J | 15 | 430 |
| XII | J | 20 | 470 |

TABLE 28

| Physical properties for each glove type | | | |
|---|---|---|---|
| Glove Type | Layers | Colour | Thickness (mm) |
| Control | Single-layered | Blue | 0.04 |
| XI | Single-layered | Metallic grey | 0.04 |
| XII | Double-layered | Metallic grey | 0.10 |

Overall migration test was carried out onto size M gloves according to standard EN 1186, using 50% ethanol as food simulant. The overall migration values of the prepared gloves were as follows:

TABLE 29

| Properties of glove | Control Glove (Formulation B) | Glove Type XI (Formulation J) | Glove Type XII (Formulation J) |
|---|---|---|---|
| Thickness (mm) | 0.04 | 0.04 | 0.10 |
| Particle (a(i)) content (%) | 0 | 13.6 | 13.6 |
| Particle (b) content (%) | 0 | 13.6 | 13.6 |

TABLE 29-continued

| Properties of glove | Control Glove (Formulation B) | Glove Type XI (Formulation J) | Glove Type XII (Formulation J) |
|---|---|---|---|
| Metal detection | No | Yes (min. 1.0 mm$^3$) | Yes (min. 1.0 mm$^3$) |
| X-ray detection | No | Yes | Yes |
| Overall migration (mg/dm$^2$) | 6.13 | 3.19 | 6.69 |

Table 29 shows overall migration values which indicate that all gloves tested were below the overall migration limit of 10 mg/dm$^2$. Interestingly, it was found that by adding detectable fillers to the glove, the migration of soluble or insoluble materials was lessened. It is postulated that, not only did the detectable particles not demonstrate any particular tendency to migrate out of the glove product, they also appeared to act as a barrier which restricted the tendency for other soluble or insoluble materials in the glove to migrate outwards. For the glove having the same thickness as the control glove, the migration level was lower, which is a positive additional effect of including particles (a) and (b) in the gloves. The thicker glove, Glove Type XII resulted in a higher migration than glove type XI, and the control glove, as the amount of material to be extracted was larger compared to the thinner gloves. Nevertheless, the migration was only slightly greater than the control glove, despite being more than twice as thick.

Gloves were also produced using an additional variation on Formulation J, with further reduced amounts of viscosity modifier (3.0 phr) and pH adjustor (0.3 phr).

Example 7—Radiation Attenuation

Gloves produced in accordance with the formulations of the examples (excluding comparative examples) have radiation attenuation properties. This provides additional functionality to the gloves.

Radiation attenuating properties of gloves can be tested in accordance with EN 61331-1. Formulation K containing multi-detectable particles was prepared at a total solid content of 40% and used to produce double-layer denoted as Glove Type XIII, which was tested according to EN 61331-1. Formulation K was used to produce gloves in accordance with this embodiment at a higher total solids content than for the prior examples, so as to produce thicker gloves suitable for use in radiation attenuation applications. For such gloves, a second coagulant dip may also be performed after the production of a first dipped layer of the elastomeric film-forming composition, and prior to a second dip into the composition, to achieve desired thickness.

The physical properties of the gloves and the test results are presented below, whereby Glove Type XIII is compared with a control glove which was produced according to Formulation B.

Formulation K: For the production of a metallic grey layer containing multi-detectable particle blend of (a(i)) and (b) based on MDP 2

TABLE 30

Formulation K: Nitrile compound with MDP 2

| Material | Amount (phr) |
|---|---|
| Nitrile latex | 100 |
| Potassium hydroxide | 1.7 |
| Ionic crosslinking agent | 0.1 |

TABLE 30-continued

Formulation K: Nitrile compound with MDP 2

| Material | Amount (phr) |
|---|---|
| (sodium aluminate) Covalent crosslinker (Sulphur) | 0.2 |
| Accelerator (ZDBC) | 0.2 |
| Antioxidant | 0.3 |
| MDP 2 – magnetite + bismuth oxide | 30 |
| Viscosity modifier (pseudoplastic acrylic based emulsion) | 2.0 |
| pH adjuster | 0.2 |

TABLE 31

Properties of composition for each glove type

| Glove Type | Formulation | Total Solid Content (%) |
|---|---|---|
| Control | B | 40 |
| XIII | K | 40 |

TABLE 32

Physical properties for each glove type

| Glove Type | Layers | Colour | Thickness (mm) | Particle (a) content (%) | Particle (c) content (%) |
|---|---|---|---|---|---|
| Control | Double-layered | Blue | 0.40 | 0 | 0 |
| XIII | Double-layered | Metallic grey | 0.38 | 6.2 | 14.6 |

Table 33

Test results for each glove type

| Glove Type | Attenuation ratio at 70 kV (%) | Attenuation ratio at 100 kV (%) | Metal detection |
|---|---|---|---|
| Control | 1.5 | 1.1 | No |
| XIII | 12.0 | 6.7 | Yes (min. 5.0 mm$^3$) |

Table 33 shows the attenuation ratio at different x-ray intensities, 70 kV and 100 kV, whereby a higher radiation intensity would normally show a lower attenuation ratio value. The multi-detectable glove type XIII had a larger tendency to attenuate radiation compared to control glove, despite having a similar thickness. The presence of particles (b) allows for a higher degree of radiation attenuation, whereas the presence of particles (a(i)) allows metal detection.

Example 8

A comparison test was performed to test the detectability of two forms of conductive particles, to assess their utility for use in the production of detectable articles (i.e. metal detector detectability). Additional work was performed to predict the performance of another type of conductive particles (tin particles) as compared to the two worked examples.

Two nitrile films were produced using a standard nitrile film formulation based on Formulation B, but without opacifying agent and blue colour, and with the addition of viscosity modifier (2 phr of pseudoplastic acrylic based emulsion) and conductive particles in accordance with Table 34 below:

TABLE 34

Properties of nitrile films containing 67% by weight conductive particles

| Film type | Film size by volume, $mm^3$ | Film density, $g/cm^3$ | Conductive particle type | Particle content (% weight) | Particle content by volume ($mm^3$) | Metal detection |
|---|---|---|---|---|---|---|
| A | 40 | 0.9 | Aluminium | 67 | 9.0 | Yes |
| B | 400 | 2.0 | Tungsten | 67 | 27.8 | No |

Gloves were produced from the two film-forming compositions of types A and B using conventional dipping techniques. Samples were cut from the gloves of types A and B having a volume of 40 $mm^3$ and 400 $mm^3$, respectively. Film A contained particles of aluminium which has a conductivity of $3.77 \times 10^7$ S/m, and Film B contained tungsten which has a conductivity of $1.79 \times 10^7$ S/m. Both materials are more conductive than tin, which has an electrical conductivity of around $0.9 \times 10^7$ S/m. Film A containing more highly conductive aluminium particles was found to be metal detectable. Film B containing lower conductivity tungsten particles was not detectable in the metal detector test, despite the high loading of particles (in weight % terms), and the high film volume tested.

The high density of tungsten (19.25 $g/cm^3$) led to a smaller volume being incorporated in the film compared to aluminium (2.7 $g/cm^3$), based on the same weight % of particles being incorporated into the film (based on total weight of the film). Taking into consideration the density of metallic tin (7.27 $g/cm^3$), as well as the density of each of films A and B (being the density of the particle-loaded films A and B, calculated by reference to the volume and weight of films A and B), and the volume of particles present in each film, estimations in terms of particle content of metallic tin in a 50 $mm^3$ film were made, and are presented in Table 35 below:

TABLE 35

Predicted properties of a film containing 67% metallic tin by weight

| Film size by volume, $mm^3$ | Conductive particle type | Particle content (% weight) | Estimated particle content by volume ($mm^3$) |
|---|---|---|---|
| 50 | Tin | 67 | 4.1-9.2 |

When making the above predictions for a film containing 67% metallic tin, it was noted that the film density of a metallic tin-containing film (based on the same polymer as used for films A and B) would be somewhere between that for films A and B, since aluminium and tungsten are at opposite ends of the spectrum for the densities of metals, and tin has a density between the aluminium and tungsten.

The films of the present application (e.g. see Films of Types I and IV films in Table 14) demonstrated detectability for volumes as low as 5.0 mm $mm^3$ and 1.0 $mm^3$. The amount of metallic tin (by volume) in a 50 $mm^3$ film, based on 67% by weight loading, is estimated to be less than the content (by volume) of tungsten in film type B which had a size of 400 $mm^3$. Since tungsten is known to be more conductive than metallic tin, it is deduced that a 50 $mm^3$ glove piece containing 67% metallic tin by weight is also not detectable (similar to the tungsten example that was subjected to the test outlined above). This contrasts to the small volumes of the films of Type I and IV outlined in Table 14, which are shown to be metal detectable. The prediction outlined above indicates that a film volume even greater than 50 $mm^3$ is required before the piece of film containing a 67 weight % loading of tin would become detectable to a metal detector. This is a very high minimum value, and outside the limits required for metal detectability required herein.

Based on this data, the applicant has deduced that for conductive particles to provide an effective means of metal detectability (either on their own, or in combination with magnetic particles), the conductive particles must have high conductivity. The conductive particles must have a conductivity of at least than $3 \times 10^7$ S/m, or electrical resistivity of less than $3 \times 10^{-8}$ $\Omega \cdot m$, both measured at 20° C. It is noted that those particles having magnetic properties together with lower conductivity below this conductivity minimum, may be selected for use in elastomeric articles for the magnetic properties (rather than conductivity properties). An example is iron, which has conductivity of $1 \times 10^7$ S/m, but can be utilised as a magnetic particulate material.

Various modifications may be made to the embodiments described in the examples without departing from the spirit and scope of the invention.

Example 9

A comparison test was performed to observe the performance of the corrosion inhibitor on corrodible magnetic particles. Two forms of iron particle dispersions of similar amounts were prepared at 60% total solids. These samples were treated with diluted acetic acid (3%) to expedite oxidation and exposed to ambient temperature of 27° C. and 50% humidity. Experiment was carried out for a week to observe for corrosion tendencies.

TABLE 36

Observation of coated and uncoated iron particles after acetic acid treatment

| Particle type | Coating type | Observation | | | |
|---|---|---|---|---|---|
| | | After 1 hour | After 24 hours | After 3 days | After 1 week |
| Coated Iron | Paraffin waxes + silane adhesion promoter | No changes in appearance | No changes in appearance | No changes in appearance | Dark brown layer on particle surfaces |

TABLE 36-continued

Observation of coated and uncoated iron particles after acetic acid treatment

| | | Observation | | | |
|---|---|---|---|---|---|
| Particle type | Coating type | After 1 hour | After 24 hours | After 3 days | After 1 week |
| Uncoated Iron | none | No changes in appearance | Formation of reddish-brown layer on particle surfaces | Increase of reddish-brown layer on particle surfaces | Increase of reddish-brown layer on particle surfaces |

From Table 36, it is shown that uncoated iron particles in presence of moisture and oxygen have a tendency to rust. An acidic environment acts as a catalyst to expedite the formation of iron oxide on the surface of the iron particle. The coating on iron serves as a barrier to minimize oxidation.

Example 10

Formulation L was prepared as follows:

TABLE 37

Formulation L: Nitrile compound with DP 6

| Material | Amount (phr) |
|---|---|
| Nitrile latex | 100 |
| Potassium hydroxide | 1.7 |
| Ionic crosslinking agent (sodium aluminate) | 0.15 |
| Ionic crosslinking agent (zinc oxide) | 0.2 |
| Covalent crosslinker (Sulphur) | 0.15 |
| Accelerator (ZDBC) | 0.2 |
| Antioxidant | 0.3 |
| DP 6 – magnetite | 16 |
| Viscosity modifier (pseudoplastic acrylic based emulsion) | 3.0 |
| pH adjuster | 0.3 |

The viscosity modifier was present in Formulation L in an amount to provide the latex composition, at a total solids content of 20%, with a viscosity of 252 cps, spindle 2, at 30 rpm.

Glove type XIV was produced from Formulation B and L, and properties were tested. The properties are summarised in the following table:

TABLE 38

Physical properties of Glove Type XIV

| Glove Type | Formulation | Layers | Colour | Thickness (mm) | Particle (a) content (%) |
|---|---|---|---|---|---|
| XIV | B and L | 2 layers (1st dip: B; 2nd dip: L) | Blue outer layer with metallic grey inner layer | 0.09 | 6.1 |

TABLE 39

Test results of Glove Type XIV

| Physical properties of glove | Glove Type XIV |
|---|---|
| Metal detection | Yes (min. 3.8 mm$^3$) |
| Tensile strength (MPa) | 25 |
| Modulus at 100% (MPa) | 1.4 |
| Modulus at 300% (MPa) | 2.6 |
| Modulus at 500% (MPa) | 6.1 |
| Elongation at break (%) | 700 |

Table 39 shows the properties of Glove type XIV which has good tensile strength while having an exceptional elongation at break of 700%.

Items:

1. An elastomeric article comprising an elastomeric film containing one or more film layers, and at least two types of particles including:
   (a) magnetic particles, and/or conductive particles having electrical conductivity of at least $3.0 \times 10^7$ S/m at 20° C., and
   (b) particles containing one or more high atomic mass elements with an atomic mass of at least 132, dispersed throughout at least one of said film layers.
2. The elastomeric article of item 1, wherein a portion of the article of 5.0 mm$^3$ or 1.0 mm$^3$ is detectable by both a metal detector and x-ray detector.
3. The elastomeric article of any one of the preceding items, in the form of a wearable article.
4. The elastomeric article of any one of the preceding items, wherein the article has a thickness in the range of 0.01 mm-3 mm.
5. The elastomeric article of any one of the preceding items, with a modulus at 500% elongation of at least 1.0 MPa.
6. The elastomeric article of any one of the preceding items, with a modulus at 500% elongation of between 1.0 and 25 MPa.
7. The elastomeric article of any one of the preceding items, with a modulus at 500% elongation of between 3.0 and 18 MPa.
8. The elastomeric article of any one of the preceding items, with a tensile strength of at least 8 MPa, or at least 12 MPa, or at least 14 MPa or at least 16 MPa.
9. The elastomeric article of any one of the preceding items, with an elongation at break of at least 100%, or at least 200%, or at least 300%, or at least 400% or at least 500%.
10. The elastomeric article of any one of the preceding items, wherein the magnetic and/or conductive particles are ferrite particles, conductive particles or a mixture thereof.
11. The elastomeric article of any one of the preceding items, wherein the article comprises said magnetic particles and the magnetic particles have an average particle size based on the mean diameter of less than 5 μm, or less than 2 μm.
12. The elastomeric article of any one of the preceding items, wherein the article comprises said magnetic particles and the magnetic particles have an average particle size based on the mean diameter by mass in the range of 0.5-1.5 μm.
13. The elastomeric article of any one of the preceding items, wherein the article comprises said conductive particles and the conductive particles have an average particle size based on the mean diameter of less than 30 μm, or less than 20 μm, or less than 15 μm.

14. The elastomeric article of any one of the preceding items, wherein the article comprises said conductive particles and the conductive particles have an average particle size based on the mean diameter by mass in the range of 0.5-11 μm.

15. The elastomeric article of any one of the preceding items, wherein the particles containing one or more high atomic mass elements are selected from the group consisting of particles of barium compounds; particles of bismuth compounds, particles of tungsten metal or tungsten compounds, or mixtures of one or more thereof.

16. The elastomeric article of any one of the preceding items, wherein the particles containing one or more high atomic mass elements have an average particle size based on the mean diameter by mass in the range of 0.1-20 μm, or 0.8-20 μm, or 0.8-15 μm.

17. The elastomeric article of any one of the preceding items, wherein the ratio of particles (a) to particles (b) is between 1:99 and 99:1.

18. The elastomeric article of any one of the preceding items, wherein the ratio of particles (a) to particles (b) is between 10:90 and 90:10.

19. The elastomeric article of any one of the preceding items, wherein the ratio of particles (a) to particles (b) is between 50:50 and 90:10.

20. The elastomeric article of any one of the preceding items, wherein the total amount of particles (a) and (b) is in the range of 2.0% and 80% by weight of the article.

21. The elastomeric article of any one of the preceding items, wherein the total amount of particles (a) and (b) is in the range of 5-50% by weight of the article.

22. The elastomeric article of any one of the preceding items, wherein the total amount of particles (a) and (b) is in the range of 10-20% by weight of the article.

23. The elastomeric article of any one of the preceding items, wherein the total amount of particles (a) and (b) is at least 2.0 phr and not more than 100 phr, such as between 5-40 phr, 5-30 phr, 10-20 phr or 5-15 phr.

24. The elastomeric article of any one of the preceding items, wherein the particles (a) and (b) are in combination and are dispersed uniformly throughout at least one film layer.

25. The elastomeric article of any one of the preceding items, wherein the particles (a) and (b) are uniformly distributed throughout each film layer of the elastomeric film in which they are each present.

26. The elastomeric article of any one of the preceding items, wherein the particles (a) and (b) are uniformly distributed throughout all film layers of the elastomeric article.

27. The elastomeric article of any one of items 1 to 25, wherein the article comprises more than one film layer, and particles (a) and (b) are uniformly distributed throughout at least one film layer, and at least one film layer is free of particles (a) and (b).

28. The elastomeric article of any one of items 1 to 23, wherein the particles (a) are uniformly distributed in one film layer, and particles (b) are uniformly distributed throughout another film layer, optionally with another layer free of particles (a) and (b).

29. The elastomeric article of any one of the preceding items, containing a viscosity modifier.

30. The elastomeric article of item 29, wherein the viscosity modifier is present in an amount sufficient to provide a composition used to prepare the elastomeric articles of between 50-1200 centipoise, using a Brookfield viscometer at 25° C., spindle no. 3, 30 rpm, measured after 24 hours.

31. The elastomeric article of item 30, wherein the amount of viscosity modifier is sufficient to provide a viscosity of the composition of between 200 and 500 centipoise.

32. The elastomeric article of any one of the preceding items, containing a multivalent metal-based cross-linking agent.

33. The elastomeric article of any one of the preceding items, wherein the elastomer is selected from the group consisting of carboxylated or non-carboxylated poly-acrylonitrile butadiene, natural rubber, polyvinyl chloride, carboxylated or non-carboxylated polychloroprene, silicone rubber, polyurethane, synthetic polyisoprene, thermoplastic elastomers and combinations or co-polymers thereof.

34. The elastomeric article of any one of the preceding items, wherein the elastomer is selected from the group consisting of carboxylated or non-carboxylated poly-acrylonitrile butadiene, natural rubber, carboxylated or non-carboxylated polychloroprene, silicone rubber, polyurethane, synthetic polyisoprene, and combinations or co-polymers thereof.

35. The elastomeric article of any one of the preceding items, wherein the elastomer is carboxylated or non-carboxylated polyacrylonitrile butadiene.

36. The elastomeric article of any one of the preceding items, wherein at least one type of particles present in the film selected from the magnetic particles, conductive particles and the particles containing one or more high atomic mass elements with an atomic mass of at least 132, are coated by a corrosion inhibitor.

37. The elastomeric article of any one of the preceding items, in the form of an unsupported glove.

38. An elastomeric film-forming composition comprising:
(a) magnetic particles and/or conductive particles having electrical conductivity of at least $3.0 \times 10^7$ S/m at 20° C., and
(b) particles containing one or more high atomic mass elements with an atomic mass of at least 132, dispersed throughout the composition.

39. The elastomeric film-forming composition of item 38, wherein the magnetic particles and/or conductive particles are ferrite particles, conductive particles or a mixture thereof.

40. The elastomeric film-forming composition of any one of items 38 to 39, wherein the composition comprises said magnetic particles and the magnetic particles have an average particle size based on the mean diameter of less than 5 μm, or less than 2 μm, or in the range of 0.5-1.5 μm.

41. The elastomeric film-forming composition of any one of items 38 to 40, wherein the composition comprises conductive particles and the conductive particles have an average particle size based on the mean diameter by mass of less than 30 μm, or less than 20 μm, or less than 15 μm, or in the range of 0.5-11 μm.

42. The elastomeric film-forming composition of any one of items 38 to 41, wherein the particles containing one or more high atomic mass elements are selected from the group consisting of particles of barium compounds, particles of bismuth compounds, particles of tungsten metal or tungsten compounds, or mixtures of one or more thereof.

43. The elastomeric film-forming composition of any one of items 38 to 42, wherein the particles containing one or more high atomic mass elements have an average particle size based on the mean diameter by mass in the range of 0.1-20 μm, or 0.8-20 μm or 0.8-15 μm.

44. The elastomeric film-forming composition of any one of items 38 to 43, wherein the ratio of particles (a) to particles (b) is between 1:99 and 99:1.

45. The elastomeric film-forming composition of any one of items 38 to 44, wherein the ratio of particles (a) to particles (b) is between 10:90 and 90:10.

46. The elastomeric film-forming composition of any one of items 38 to 45, wherein the ratio of particles (a) to particles (b) is between 50:50 and 90:10.

47. The elastomeric film-forming composition of any one of items 38 to 46, wherein the total amount of particles (a) and (b) is at least 2.0 phr and not more than 100 phr, such as between 5-40 phr, 5-30 phr, 10-20 phr or 5-15 phr.

48. The elastomeric film-forming composition of any one of items 38 to 47, wherein the total amount of particles (a) and (b) is between 0.1% and 10% by weight of the elastomeric film-forming composition.

49. The elastomeric film-forming composition of any one of items 38 to 48, comprising a viscosity modifier.

50. The elastomeric film-forming composition of item 49, wherein the viscosity modifier is present in an amount sufficient to provide the composition with a viscosity of between 50-1200 centipoise using a Brookfield viscometer at 25° C., spindle no. 3, 30 rpm, measured after 24 hours.

51. The elastomeric film-forming composition of item 50, wherein the amount of viscosity modifier is sufficient to provide the composition with a viscosity of between 200 and 500 centipoise.

52. The elastomeric film-forming composition of any one of items 38 to 51, containing a multivalent metal-based cross-linking agent.

53. The elastomeric film-forming composition of any one of items 38 to 52, comprising an elastomer selected from the group consisting of carboxylated or non-carboxylated polyacrylonitrile butadiene, natural rubber, polyvinyl chloride, carboxylated or non-carboxylated polychloroprene, silicone rubber, polyurethane, synthetic polyisoprene, thermoplastic elastomers and combinations or co-polymers thereof.

54. The elastomeric film-forming composition of any one of items 38 to 52, comprising an elastomer selected from the group consisting of carboxylated or non-carboxylated polyacrylonitrile butadiene, natural rubber, carboxylated or non-carboxylated polychloroprene, silicone rubber, polyurethane, synthetic polyisoprene, thermoplastic elastomers and combinations or co-polymers thereof.

55. The elastomeric film-forming composition of any one of items 38 to 54, having a total solids content between 5 and 50%, or between 5% and 40%.

56. The elastomeric film-forming composition of any one of items 38 to 56, wherein at least one type of particles present in the film selected from the magnetic particles, the conductive particles and the particles containing one or more high atomic mass elements with an atomic mass of at least 132, are coated by corrosion inhibitor.

57. The elastomeric film-forming composition of any one of items 38 to 56, wherein the composition comprises said magnetic particles, and the composition further comprising an anti-corrosive material in the elastomeric film-forming composition.

58. A method of manufacturing the elastomeric article of any one of items 1 to 37, the method comprising:
incorporating (a) magnetic particles and/or conductive particles having electrical conductivity of at least $3.0 \times 10^7$ S/m at 20° C., and (b) particles containing one or more high atomic mass elements with an atomic mass of at least 132, into one or more elastomeric film-forming compositions, and
dipping a former into the or each of said one or more elastomeric film-forming compositions, to produce an article comprising one or more film layers, in which (a) the magnetic particles and/or the conductive particles and (b) the particles containing one or more high atomic mass elements, are dispersed throughout at least one of said film layers.

59. The method of item 58, comprising:
dipping the former into an elastomeric film-forming composition of any one of items 38 to 57; and
curing the elastomeric film-forming composition on the former so as to produce the elastomeric article.

60. An elastomeric article comprising an elastomeric film containing one or more film layers, wherein at least one film layer comprises:
at least one type of particles selected from (a(i)) magnetic particles, (a(ii)) conductive particles having electrical conductivity of at least $3.0 \times 10^7$ S/m at 20° C. and/or (b) particles containing one or more high atomic mass elements dispersed throughout the film layer, and
a pseudoplastic viscosity modifier for achieving the dispersion of said particles throughout the film layer.

61. The elastomeric article of item 60 wherein the article comprises said magnetic particles.

62. The elastomeric article of item 61, wherein the magnetic particles have an average particle size based on the mean diameter of less than 5 μm, or less than 2 μm.

63. The elastomeric article of any one of items 60 to 62, wherein the particles are coated by a corrosion inhibitor.

64. The elastomeric article of any one of items 60 to 63, wherein a portion of the article of 5.0 mm³ or 1.0 mm³ is detectable by a metal detector.

65. The elastomeric article of any one of items 60 to 64, wherein the article has a thickness in the range of 0.01 mm-3 mm.

66. The elastomeric article of any one items 60 to 65, with a modulus at 500% elongation of between 1.0 and 25 MPa.

67. The elastomeric article of any one items 60 to 66, with an elongation at break of at least 100%, or at least 200%, or at least 300%, or at least 400% or at least 500%.

68. The elastomeric article of any one items 60 to 67, wherein the total amount of said particles is in the range of 2.0% and 80% by weight of the article.

69. The elastomeric article of any one items 60 to 68, wherein the elastomer is selected from the group consisting of carboxylated or non-carboxylated polyacrylonitrile butadiene, natural rubber, polyvinyl chloride, carboxylated or non-carboxylated polychloroprene, silicone rubber, polyurethane, synthetic polyisoprene, thermoplastic elastomers and combinations or co-polymers thereof.

70. The elastomeric article of any one of items 60 to 69, wherein the pseudoplastic viscosity modifier is a non-associative thickener.

71. An elastomeric film-forming composition comprising:
    at least one type of particles selected from (a(i)) magnetic particles, (a(ii)) conductive particles having electrical conductivity of at least $3.0 \times 10^7$ S/m at 20° C. and/or (b) particles containing one or more high atomic mass elements, and
    a pseudoplastic viscosity modifier for dispersing said particles throughout the composition.

72. The elastomeric film-forming composition of item 71, wherein the viscosity modifier is present in an amount sufficient to provide the composition with a viscosity of between 50-1200 centipoise using a Brookfield viscometer at 25° C., spindle no. 3, 30 rpm, measured after 24 hours.

73. The elastomeric film-forming composition of item 71 or item 72, wherein the composition comprises said magnetic particles.

74. The elastomeric film-forming composition of item 73, wherein the magnetic particles have an average particle size based on the mean diameter of less than 5 μm, or less than 2 μm.

75. The elastomeric film-forming composition of any one of items 71 to 74, wherein the particles are coated by a corrosion inhibitor.

76. The elastomeric film-forming composition of any one of items 71 to 75, comprising an elastomer selected from the group consisting of carboxylated or non-carboxylated polyacrylonitrile butadiene, natural rubber, polyvinyl chloride, carboxylated or non-carboxylated polychloroprene, silicone rubber, polyurethane, synthetic polyisoprene, thermoplastic elastomers and combinations or co-polymers thereof.

77. The elastomeric film-forming composition of any one of items 71 to 76, wherein the pseudoplastic viscosity modifier is a non-associative thickener.

78. A method for the production of the elastomeric article of any one of items 60 to 70, the method comprising:
    combining at least one type of particles selected from (a(i)) magnetic particles, (a(ii)) conductive particles having electrical conductivity of at least $3.0 \times 10^7$ S/m at 20° C. and/or (b) particles containing one or more high atomic mass elements, and a pseudoplastic viscosity modifier in an elastomeric article-forming composition so as to effect dispersion of said particles throughout the composition;
    dipping a former into said elastomeric film-forming composition; and
    curing the elastomeric film-forming composition on the former so as to produce the elastomeric article.

79. The method of item 79, further comprising:
    stirring the elastomeric film-forming composition in a dipping tank so as to maintain the viscosity of the composition during dipping of the former into the composition at a level that is lower than that for the unstirred elastomeric film-forming composition.

80. The method of item 78 or item 79, wherein the composition comprises said magnetic particles.

81. The method of item 80, wherein the magnetic particles have an average particle size based on the mean diameter of less than 5 μm, or less than 2 μm.

82. The method of any one of items 78 to 81, wherein the particles are coated by a corrosion inhibitor.

83. The method of any one of items 78 to 82, wherein the elastomer is selected from the group consisting of carboxylated or non-carboxylated polyacrylonitrile butadiene, natural rubber, polyvinyl chloride, carboxylated or non-carboxylated polychloroprene, silicone rubber, polyurethane, synthetic polyisoprene, thermoplastic elastomers and combinations or co-polymers thereof.

84. The method of any one of items 78 to 83, wherein the pseudoplastic viscosity modifier is present in an amount sufficient to provide the composition with a viscosity of between 50-1200 centipoise using a Brookfield viscometer at 25° C., spindle no. 3, 30 rpm, measured after 24 hours.

85. The method of any one of items 78 to 84, wherein the pseudoplastic viscosity modifier is a non-associative thickener.

86. An elastomeric article comprising an elastomeric film containing one or more film layers, wherein at least one film layer comprises magnetic particles dispersed throughout the film layer, wherein the magnetic particles are coated by a corrosion inhibitor, and/or a corrosion inhibitor is dispersed throughout said film layer containing the magnetic particles.

87. The elastomeric article of item 86, wherein the magnetic particles are coated by a corrosion inhibitor.

88. The elastomeric article of item 87, wherein the corrosion inhibitor is selected from the group consisting of silicones, waxes, polymers, corrosion-resistant metal salts and corrosion-resistant metals, or a combination thereof.

89. The elastomeric article of any one of items 86 to 88, further comprising a functional layer between a magnetic particle core and the corrosion inhibitor coating.

90. The elastomeric article of any one of items 86 to 89, wherein the amount of corrosion-inhibitor coated magnetic particles is between about 2% and 80% by weight of the article, or between 2-50%, 2-40%, 2-30%, 2-20%, 5-50%, 5-40%, 5-30%, 5-20%, 10-50%, 10-40%, or 10-30% by weight of the article.

91. The elastomeric article of any one of items 86 to 90, wherein the magnetic particles have an average particle size based on the mean diameter of less than 5 μm, or less than 2 μm.

92. The elastomeric article of any one of items 86 to 91, wherein a portion of the article of 5.0 $mm^3$ or 1.0 $mm^3$ is detectable by a metal detector.

93. The elastomeric article of any one of items 86 to 92, wherein the article has a thickness in the range of 0.01 mm-3 mm.

94. The elastomeric article of any one items 86 to 93, with a modulus at 500% elongation of between 1.0 and 25 MPa.

95. The elastomeric article of any one items 86 to 94, with an elongation at break of at least 100%, or at least 200%, or at least 300%, or at least 400% or at least 500%.

96. The elastomeric article of any one items 86 to 95, wherein the elastomer is selected from the group consisting of carboxylated or non-carboxylated polyacrylonitrile butadiene, natural rubber, polyvinyl chloride, carboxylated or non-carboxylated polychloroprene, silicone rubber, polyurethane, synthetic polyisoprene, thermoplastic elastomers and combinations or co-polymers thereof.

97. The elastomeric article of any one of items 86 to 96 further comprising:
    conductive particles having electrical conductivity of at least $3.0 \times 10^7$ S/m at 20° C., and/or particles containing one or more high atomic mass elements with an atomic mass of at least 132, dispersed throughout at least one of said film layers.

98. The elastomeric article of any one of items 86 to 97, comprising a viscosity modifier.

99. An elastomeric film-forming composition comprising magnetic particles, wherein the magnetic particles are coated by a corrosion inhibitor, and/or a corrosion inhibitor is dispersed throughout said film composition.

100. The elastomeric film-forming composition of item 99, wherein the magnetic particles are coated by a corrosion inhibitor.

101. The elastomeric film-forming composition of item 100, wherein the corrosion inhibitor is selected from the group consisting of silicones, waxes, polymers, corrosion-resistant metal salts and corrosion-resistant metals, or a combination thereof.

102. The elastomeric film-forming composition of any one of items 100 to 101, further comprising a functional layer between a magnetic particle core and the corrosion inhibitor coating.

103. The elastomeric film-forming composition of any one of items 100 to 102, wherein the amount of corrosion-inhibitor coated magnetic particles is between about 2% and 80% by weight of the article.

104. The elastomeric film-forming composition of any one of items 100 to 103, wherein the magnetic particles have an average particle size based on the mean diameter of less than 5 μm, or less than 2 μm.

105. The elastomeric film-forming composition of any one of items 99 to 104, further comprising a viscosity modifier 106. The elastomeric film-forming composition of item 105, wherein the viscosity modifier is present in an amount sufficient to provide the composition with a viscosity of between 50-1200 centipoise using a Brookfield viscometer at 25° C., spindle no. 3, 30 rpm, measured after 24 hours.

107. The elastomeric film-forming composition of any one of items 99 to 106, comprising an elastomer selected from the group consisting of carboxylated or non-carboxylated polyacrylonitrile butadiene, natural rubber, polyvinyl chloride, carboxylated or non-carboxylated polychloroprene, silicone rubber, polyurethane, synthetic polyisoprene, thermoplastic elastomers and combinations or co-polymers thereof.

108. A method for the production of the elastomeric article of any one of items 86 to 98, the method comprising:

dipping a former into the elastomeric film-forming composition of any one of items 99 to 107; and curing the elastomeric film-forming composition on the former so as to produce the elastomeric article.

109. An elastomeric article comprising an elastomeric film containing one or more film layers, wherein at least one film layer comprises magnetic particles coated by a corrosion inhibitor, dispersed throughout the film layer.

110. An elastomeric article comprising an elastomeric film containing one or more film layers, wherein at least one film layer comprises magnetic particles and a corrosion inhibitor dispersed throughout the film layer, wherein the corrosion inhibitor inhibits corrosion of the magnetic particles in the film.

111. An elastomeric article as produced by the method of any one of items 58, 59, 78 to 85 or 108.

112. Use of the composition of any one of items 38 to 57, 71-77 or 99 to 107 for the production of multi-detectable wearable articles that is detectable by metal detector and x-ray detector.

113. Use of the elastomeric article of any one of items 1 to 37, 60 to 70 or 86 to 98 as a metal detectable, x-ray detectable and a radiation-attenuating article.

The invention claimed is:

1. A dipped elastomeric article comprising an elastomeric film with a thickness in the range of 0.01-2.0 mm, the elastomeric film containing one or more film layers, wherein at least one film layer comprises:

at least one type of particles selected from:

(a(i)) magnetic particles, wherein the magnetic particles are selected from the group consisting of ferromagnetic particles based on at least one of iron, nickel, and cobalt, and ferrimagnetic particles; and (a(ii)) conductive particles having electrical conductivity of at least $3.0 \times 10^7$ S/m at 20° C. dispersed throughout the film layer, and a pseudoplastic viscosity modifier for achieving the dispersion of said particles throughout the film layer, wherein:

the particles are coated by a corrosion inhibitor and/or a corrosion inhibitor is dispersed throughout said film layer, said corrosion inhibitor being selected from the group consisting of silicones, waxes, corrosion-inhibiting polymers, corrosion-resistant metal salts, corrosion-resistant metals and combinations thereof;

each of said one or more film layers is formed by dipping a former into a film-forming composition having a total solids content of between 5 and 50% which comprises:

(b(i)) an elastomer-forming polymer consisting of nitrile rubber, or non-carboxylated polychloroprene, or a combination thereof; and (b(ii)) a cross-linking agent, so as to produce said elastomeric film with the thickness in the range of 0.01-2 mm; and the dipped elastomeric article has:

(c(i)) a modulus at 500% elongation of between 1.0 and 25 MPa; and (c(ii)) an elongation at break of at least 100%.

2. The dipped elastomeric article of claim 1, wherein the article comprises said magnetic particles.

3. The dipped elastomeric article of claim 2, wherein the magnetic particles have an average particle size based on the mean diameter of less than 5 μm.

4. The dipped elastomeric article of claim 1, wherein a portion of the article of 5.0 mm³ or 1.0 mm³ in size is detectable by a metal detector.

5. The dipped elastomeric article of claim 1, wherein the article has a thickness in the range of 0.01 mm-1 mm.

6. The dipped elastomeric article of claim 1, wherein the total amount of said particles is in the range of 2.0% and 80% by weight of the article.

7. The dipped elastomeric article of claim 1, wherein the pseudoplastic viscosity modifier is a non-associative thickener.

8. The dipped elastomeric article of claim 1, further comprising particles containing one or more high atomic mass elements dispersed throughout at least one of said film layers.

9. The dipped elastomeric article of claim 2, wherein the magnetic particles are ferrimagnetic particles.

10. The dipped elastomeric article of claim 2, wherein the magnetic particles are magnetite particles.

11. The dipped elastomeric article of claim 1, wherein the elastomer-forming polymer consists of nitrile rubber.

12. The dipped elastomeric article of claim 1, wherein the magnetic particles have an average particle size based on the mean diameter of from 0.5 μm to 1.5 μm, and/or the conductive particles have an average particle size based on the mean diameter of from 0.5 μm to 12 μm.

13. The dipped elastomeric article of claim 1, wherein the pseudoplastic viscosity modifier is present in an amount of from 0.5 to 10 phr.

14. A dipped elastomeric article comprising an elastomeric film with a thickness in the range of 0.01-2.0 mm, the elastomeric film containing one or more film layers, wherein at least one film layer comprises magnetic particles dispersed throughout the film layer, wherein the magnetic particles are coated by a corrosion inhibitor, and the magnetic particles are selected from the group consisting of ferromagnetic particles based on at least one of iron, nickel, and cobalt, and ferrimagnetic particles, wherein:

the corrosion inhibitor is selected from the group consisting of silicones, waxes, corrosion-inhibiting polymers, corrosion-resistant metal salts, corrosion-resistant metals and combinations thereof;

each of said one or more film layers is formed by dipping a former into a film-forming composition having a total solids content of between 5 and 50% which comprises:

(a(i)) an elastomer-forming polymer consisting of nitrile rubber, or non-carboxylated polychloroprene, or a combination thereof; and (a(ii)) a cross-linking agent, so as to produce said elastomeric film with the thickness in the range of 0.01-2.0 mm; and the dipped elastomeric article has:

(b(i)) a modulus at 500% elongation of between 1.0 and 25 MPa; and (b(ii)) an elongation at break of at least 100%.

15. The dipped elastomeric article of claim 14, wherein the magnetic particles have an average particle size based on the mean diameter of less than 5 μm.

16. The dipped elastomeric article of claim 14, wherein a portion of the article of 5.0 mm$^3$ or 1.0 mm$^3$ in size is detectable by a metal detector.

\* \* \* \* \*